United States Patent [19]
Reed

[11] Patent Number: 5,876,966
[45] Date of Patent: Mar. 2, 1999

[54] COMPOUNDS AND METHODS FOR THE STIMULATION AND ENHANCEMENT OF PROTECTIVE IMMUNE RESPONSES AND IL-12 PRODUCTION

[75] Inventor: Steven G. Reed, Bellevue, Wash.

[73] Assignee: Corixa Corporation, Seattle, Wash.

[21] Appl. No.: 454,036

[22] Filed: May 30, 1995

Related U.S. Application Data

[63] Continuation-in-part of Ser. No. 232,534, Apr. 22, 1994, abandoned.

[51] Int. Cl.$^6$ .......................... A61K 39/00; A61K 39/02; C07K 1/00; C07H 21/02
[52] U.S. Cl. .................. 435/69.3; 424/184.1; 424/234.1; 424/265.1; 424/269.1; 536/23.1; 536/23.7; 530/350
[58] Field of Search .............................. 424/184.1, 234.1, 424/265.1, 269.1; 530/350; 435/69.3; 536/23.1, 23.7

[56] References Cited

PUBLICATIONS

Skeiky et al. J. Exp. Med. 181:1527–1537, 1995.
Metz et al. Gene 120:313–314, 1992.
Y.A.W. Skeiky et al., "Proliferative and Cytokine Responses of Human PBMC to Cloned *Leishmania Brazilienis* Heat Shock and Ribosomal Antigens," *Journal of Immunology* 150(8):93a., 1993.
S.L. Reiner et al., "Leishmania Promastigotes Evade Interleukin 12 (IL–12) Induction by Macrophages and Stimulate a Broad Range of Cytokines from CD4+ T Cells During Initiation of Infection," *J. Exp. Med.* 179(2):447–456, 1994.
F.P. Heinzel et al., "Recombinant Interleukin–12 Cures Mice Infected with *Leishmania major*," *J. Exp. Med.* 177(5):1505–1509, 1993.
J.P. Sypek et al., "Resolution of Cutaneous Leishmaniasis: Interleukin–12 Initiates a Protective T Helper Type 1 Immune Response," *J. Exp. Med.* 177(6):1797–1802, 1993.
L.C.C. Afonso et al., "The Adjuvant Effect of Interleukin–12 in a Vaccine Against *Leishmania major*," *Science* 263:235–237, 1994.
S. G. Reed et al., "T–Cell and Cytokine Responses in Leishmaniasis," *Current Opinion in Immunology* 5(4):524–531, 1993.
Y.A.W. Skeiky et al., "A Recombinant *Leishmania* Antigen that Stimulates Human Peripheral Blood Mononuclear Cells to Express a Th1–Type Cytokine Profile and to Produce Interleukin 12," *J. Exp. Med.* 181:1527–1537, 1995.
G. Trinchieri, "Interleukin–12 and its Role in the Generation of $T_H1$ Cells," *Immunology Today* 14(7):335–338, 1993.
Ghalib et al., "IL–12 Enhances Th1–Type Responses in Human *Leishmania donovani* Infections," *J. Immunol.* 154(9):4623–4629, 1995.

*Primary Examiner*—James C. Housel
*Assistant Examiner*—V. Ryan
*Attorney, Agent, or Firm*—Seed and Berry LLP

[57] ABSTRACT

Compounds and methods for stimulating and enhancing immune responses and for evaluating patient immune responses are disclosed. Disclosed compounds include polypeptides that contain at least a biologically active portion of a *Leishmania braziliensis* homolog of the eukaryotic initiation factor 4A, or a variant thereof. Such compounds are useful for stimulating a Th1 immune response and IL-12 production in patients, as well as in isolated cells and cell cultures. The polypeptides of this invention are further useful for the evaluation and treatment of patients, who may be afflicted with leishmaniasis or other disorders.

3 Claims, 14 Drawing Sheets

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
  ( A ) LENGTH: 1618 base pairs
  ( B ) TYPE: nucleic acid
  ( C ) STRANDEDNESS: single
  ( D ) TOPOLOGY: linear ( i i ) MOLECULE TYPE: cDNA ( i x ) FEATURE:
  ( A ) NAME/KEY: CDS
  ( B ) LOCATION: 115..1326

( x i ) SEQUENCE DESCRIPTION: SEQ ID NO:1:

```
CCACTCTCTC  GGTCGTCTGT  CTCCCACGCG  CGCACGCAGT  TGATTTCCGC  CTTCTTAAAC         60

GCTCTCTTTT  TTTTTATTTT  TCACCTGACC  AACCGCACCA  CGTCGGCCTC  CATC ATG         117
                                                                Met
                                                                  1

TCG  CAG  CAA  GAC  CGA  GTT  GCC  CCA  CAG  GAC  CAG  GAC  TCG  TTC  CTC  GAC    165
Ser  Gln  Gln  Asp  Arg  Val  Ala  Pro  Gln  Asp  Gln  Asp  Ser  Phe  Leu  Asp
               5                      10                     15

GAC  CAG  CCC  GGC  GTC  CGC  CCG  ATC  CCG  TCC  TTC  GAT  GAC  ATG  CCG  TTG    213
Asp  Gln  Pro  Gly  Val  Arg  Pro  Ile  Pro  Ser  Phe  Asp  Asp  Met  Pro  Leu
              20                      25                     30

CAC  CAG  AAC  CTT  CTG  CGC  GGC  ATC  TAC  TCG  TAC  GGC  TTC  GAG  AAA  CCG    261
His  Gln  Asn  Leu  Leu  Arg  Gly  Ile  Tyr  Ser  Tyr  Gly  Phe  Glu  Lys  Pro
              35                      40                     45

TCC  AGC  ATC  CAG  CAG  CGC  GCC  ATC  GCC  CCC  TTC  ACG  CGC  GGC  GGC  GAC    309
Ser  Ser  Ile  Gln  Gln  Arg  Ala  Ile  Ala  Pro  Phe  Thr  Arg  Gly  Gly  Asp
```

-continued

| | | | | | | | | | | | | | | | | |
|---|---|---|---|---|---|---|---|---|---|---|---|---|---|---|---|---|
| 50 | | | | | 55 | | | | | 60 | | | | | 65 | |
| ATC | ATC | GCG | CAG | GCG | CAG | TCC | GGT | ACC | GGC | AAG | ACG | GGC | GCC | TTC | TCC | 357 |
| Ile | Ile | Ala | Gln | Ala | Gln | Ser | Gly | Thr | Gly | Lys | Thr | Gly | Ala | Phe | Ser | |
| | | | 70 | | | | | 75 | | | | | 80 | | | |
| ATC | GGC | CTG | CTG | CAG | CGC | CTG | GAC | TTC | CGC | CAC | AAC | CTG | ATC | CAG | GGC | 405 |
| Ile | Gly | Leu | Leu | Gln | Arg | Leu | Asp | Phe | Arg | His | Asn | Leu | Ile | Gln | Gly | |
| | | | 85 | | | | | 90 | | | | | 95 | | | |
| CTC | GTG | CTC | TCC | CCG | ACC | CGC | GAG | CTG | GCC | CTG | CAG | ACG | GCG | GAG | GTG | 453 |
| Leu | Val | Leu | Ser | Pro | Thr | Arg | Glu | Leu | Ala | Leu | Gln | Thr | Ala | Glu | Val | |
| | | 100 | | | | | 105 | | | | | 110 | | | | |
| ATC | AGC | CGC | ATC | GGC | GAG | TTC | CTG | TCG | AAC | AGC | GCG | AAG | TTC | TGT | GAG | 501 |
| Ile | Ser | Arg | Ile | Gly | Glu | Phe | Leu | Ser | Asn | Ser | Ala | Lys | Phe | Cys | Glu | |
| | | 115 | | | | | 120 | | | | | 125 | | | | |
| ACC | TTT | GTG | GGT | GGC | ACG | CGC | GTG | CAG | GAT | GAC | CTG | CGC | AAG | CTG | CAG | 549 |
| Thr | Phe | Val | Gly | Gly | Thr | Arg | Val | Gln | Asp | Asp | Leu | Arg | Lys | Leu | Gln | |
| 130 | | | | | 135 | | | | | 140 | | | | | 145 | |
| GCT | GGC | GTC | GTC | GTC | GCC | GTG | GGG | ACG | CCG | GGC | CGC | GTG | TCC | GAC | GTG | 597 |
| Ala | Gly | Val | Val | Val | Ala | Val | Gly | Thr | Pro | Gly | Arg | Val | Ser | Asp | Val | |
| | | | | 150 | | | | | 155 | | | | | 160 | | |
| ATC | AAG | CGC | GGC | GCG | CTG | CGC | ACC | GAG | TCC | CTG | CGC | GTG | CTG | GTG | CTC | 645 |
| Ile | Lys | Arg | Gly | Ala | Leu | Arg | Thr | Glu | Ser | Leu | Arg | Val | Leu | Val | Leu | |
| | | | 165 | | | | | 170 | | | | | 175 | | | |
| GAC | GAG | GCT | GAT | GAG | ATG | CTG | TCT | CAG | GGC | TTC | GCG | GAT | CAG | ATT | TAC | 693 |
| Asp | Glu | Ala | Asp | Glu | Met | Leu | Ser | Gln | Gly | Phe | Ala | Asp | Gln | Ile | Tyr | |
| | | 180 | | | | | 185 | | | | | 190 | | | | |
| GAG | ATC | TTC | CGC | TTC | CTG | CCG | AAG | GAC | ATC | CAG | GTC | GCG | CTC | TTC | TCC | 741 |
| Glu | Ile | Phe | Arg | Phe | Leu | Pro | Lys | Asp | Ile | Gln | Val | Ala | Leu | Phe | Ser | |
| | 195 | | | | | 200 | | | | | 205 | | | | | |
| GCC | ACG | ATG | CCG | GAG | GAG | GTG | CTG | GAG | CTG | ACA | AAG | AAG | TTC | ATG | CGC | 789 |
| Ala | Thr | Met | Pro | Glu | Glu | Val | Leu | Glu | Leu | Thr | Lys | Lys | Phe | Met | Arg | |
| 210 | | | | | 215 | | | | | 220 | | | | | 225 | |
| GAC | CCC | GTA | CGC | ATT | CTC | GTG | AAG | CGC | GAG | AGC | CTG | ACG | CTG | GAG | GGC | 837 |
| Asp | Pro | Val | Arg | Ile | Leu | Val | Lys | Arg | Glu | Ser | Leu | Thr | Leu | Glu | Gly | |
| | | | | 230 | | | | | 235 | | | | | 240 | | |
| ATC | AAG | CAG | TTC | TTC | ATC | GCC | GTC | GAG | GAG | GAG | CAC | AAG | CTG | GAC | ACG | 885 |
| Ile | Lys | Gln | Phe | Phe | Ile | Ala | Val | Glu | Glu | Glu | His | Lys | Leu | Asp | Thr | |
| | | | 245 | | | | | 250 | | | | | 255 | | | |
| CTG | ATG | GAC | CTG | TAC | GAG | ACC | GTG | TCC | ATC | GCG | CAG | TCC | GTC | ATC | TTC | 933 |
| Leu | Met | Asp | Leu | Tyr | Glu | Thr | Val | Ser | Ile | Ala | Gln | Ser | Val | Ile | Phe | |
| | | 260 | | | | | 265 | | | | | 270 | | | | |
| GCC | AAC | ACC | CGC | CGC | AAG | GTG | GAC | TGG | ATC | GCC | GAG | AAG | CTG | AAT | CAG | 981 |
| Ala | Asn | Thr | Arg | Arg | Lys | Val | Asp | Trp | Ile | Ala | Glu | Lys | Leu | Asn | Gln | |
| | 275 | | | | | 280 | | | | | 285 | | | | | |
| AGC | AAC | CAC | ACC | GTC | AGC | AGC | ATG | CAC | GCC | GAG | ATG | CCC | AAG | AGC | GAC | 1029 |
| Ser | Asn | His | Thr | Val | Ser | Ser | Met | His | Ala | Glu | Met | Pro | Lys | Ser | Asp | |
| 290 | | | | | 295 | | | | | 300 | | | | | 305 | |
| CGC | GAG | CGC | GTC | ATG | AAC | ACC | TTC | CGC | AGC | GGC | AGC | TCC | CGC | GTG | CTC | 1077 |
| Arg | Glu | Arg | Val | Met | Asn | Thr | Phe | Arg | Ser | Gly | Ser | Ser | Arg | Val | Leu | |
| | | | | 310 | | | | | 315 | | | | | 320 | | |
| GTA | ACG | ACC | GAC | CTC | GTG | GCC | CGC | GGC | ATC | GAC | GTG | CAC | CAC | GTG | AAC | 1125 |
| Val | Thr | Thr | Asp | Leu | Val | Ala | Arg | Gly | Ile | Asp | Val | His | His | Val | Asn | |
| | | | 325 | | | | | 330 | | | | | 335 | | | |
| ATC | GTC | ATC | AAC | TTC | GAC | CTG | CCG | ACG | AAC | AAG | GAG | AAC | TAC | CTG | CAC | 1173 |
| Ile | Val | Ile | Asn | Phe | Asp | Leu | Pro | Thr | Asn | Lys | Glu | Asn | Tyr | Leu | His | |
| | | 340 | | | | | 345 | | | | | 350 | | | | |
| CGC | ATT | GGC | CGC | GGC | GGC | CGC | TAC | GGC | GTA | AAG | GGT | GTT | GCC | ATC | AAC | 1221 |
| Arg | Ile | Gly | Arg | Gly | Gly | Arg | Tyr | Gly | Val | Lys | Gly | Val | Ala | Ile | Asn | |
| | 355 | | | | | 360 | | | | | 365 | | | | | |
| TTC | GTG | ACG | GAG | AAA | GAC | GTG | GAG | CTG | CTG | CAC | GAG | ATC | GAG | GGG | CAC | 1269 |
| Phe | Val | Thr | Glu | Lys | Asp | Val | Glu | Leu | Leu | His | Glu | Ile | Glu | Gly | His | |

-continued

```
      370                    375                    380                     385
TAC  CAC  ACG  CAG  ATC  GAT  GAG  CTC  CCG  GTG  GAC  TTT  GCC  GCC  TAC  CTC    1317
Tyr  His  Thr  Gln  Ile  Asp  Glu  Leu  Pro  Val  Asp  Phe  Ala  Ala  Tyr  Leu
                    390                    395                     400

GGC  GAG  TGA  GCGGGCCCCT  GCCCCCTTC   CCTGCCCCC   TCTCGCGACG                     1366
Gly  Glu   *
AGAGAACGCA  CATCGTAACA  CAGCCACGCG  AACGATAGTA  AGGGCGTGCG  GCGGCGTTCC           1426

CCTCCTCCTG  CCAGCGGCCC  CCCTCCGCAG  CGCTTCTCTT  TTGAGAGGGG  GGCAGGGGA            1486

GGCGCTGCGC  CTGGCTGGAT  GTGTGCTTGA  GCTTGCATTC  CGTCAAGCAA  GTGCTTTGTT           1546

TTAATTATGC  GCGCCGTTTT  GTTGCTCGTC  CCTTTCGTTG  GTGTTTTTTC  GGCCGAAACG           1606

GCGTTTAAAG  CA                                                                    1618
```

(2) INFORMATION FOR SEQ ID NO:2:

(i) SEQUENCE CHARACTERISTICS:
        (A) LENGTH: 403 amino acids
        (B) TYPE: amino acid
        (D) TOPOLOGY: linear (ii) MOLECULE TYPE: protein (xi) SEQUENCE DESCRIPTION: SEQ ID NO:2:

```
Met  Ser  Gln  Gln  Asp  Arg  Val  Ala  Pro  Gln  Asp  Gln  Asp  Ser  Phe  Leu
 1                  5                        10                      15

Asp  Asp  Gln  Pro  Gly  Val  Arg  Pro  Ile  Pro  Ser  Phe  Asp  Asp  Met  Pro
                20                       25                      30

Leu  His  Gln  Asn  Leu  Leu  Arg  Gly  Ile  Tyr  Ser  Tyr  Gly  Phe  Glu  Lys
                35                       40                      45

Pro  Ser  Ser  Ile  Gln  Gln  Arg  Ala  Ile  Ala  Pro  Phe  Thr  Arg  Gly  Gly
                50                       55                      60

Asp  Ile  Ile  Ala  Gln  Ala  Gln  Ser  Gly  Thr  Gly  Lys  Thr  Gly  Ala  Phe
 65                      70                       75                      80

Ser  Ile  Gly  Leu  Leu  Gln  Arg  Leu  Asp  Phe  Arg  His  Asn  Leu  Ile  Gln
                     85                       90                      95

Gly  Leu  Val  Leu  Ser  Pro  Thr  Arg  Glu  Leu  Ala  Leu  Gln  Thr  Ala  Glu
                100                      105                     110

Val  Ile  Ser  Arg  Ile  Gly  Glu  Phe  Leu  Ser  Asn  Ser  Ala  Lys  Phe  Cys
                115                      120                     125

Glu  Thr  Phe  Val  Gly  Gly  Thr  Arg  Val  Gln  Asp  Asp  Leu  Arg  Lys  Leu
     130                      135                     140

Gln  Ala  Gly  Val  Val  Val  Ala  Val  Gly  Thr  Pro  Gly  Arg  Val  Ser  Asp
145                      150                      155                     160

Val  Ile  Lys  Arg  Gly  Ala  Leu  Arg  Thr  Glu  Ser  Leu  Arg  Val  Leu  Val
                     165                      170                     175

Leu  Asp  Glu  Ala  Asp  Glu  Met  Leu  Ser  Gln  Gly  Phe  Ala  Asp  Gln  Ile
                180                      185                     190

Tyr  Glu  Ile  Phe  Arg  Phe  Leu  Pro  Lys  Asp  Ile  Gln  Val  Ala  Leu  Phe
                195                      200                     205

Ser  Ala  Thr  Met  Pro  Glu  Glu  Val  Leu  Glu  Leu  Thr  Lys  Lys  Phe  Met
     210                      215                     220

Arg  Asp  Pro  Val  Arg  Ile  Leu  Val  Lys  Arg  Glu  Ser  Leu  Thr  Leu  Glu
225                      230                      235                     240

Gly  Ile  Lys  Gln  Phe  Phe  Ile  Ala  Val  Glu  Glu  His  Lys  Leu  Asp
                     245                      250                     255

Thr  Leu  Met  Asp  Leu  Tyr  Glu  Thr  Val  Ser  Ile  Ala  Gln  Ser  Val  Ile
                260                      265                     270
```

```
Phe Ala Asn Thr Arg Arg Lys Val Asp Trp Ile Ala Glu Lys Leu Asn
        275                 280              285
Gln Ser Asn His Thr Val Ser Ser Met His Ala Glu Met Pro Lys Ser
    290             295              300
Asp Arg Glu Arg Val Met Asn Thr Phe Arg Ser Gly Ser Ser Arg Val
305             310              315                      320
Leu Val Thr Thr Asp Leu Val Ala Arg Gly Ile Asp Val His His Val
            325              330                      335
Asn Ile Val Ile Asn Phe Asp Leu Pro Thr Asn Lys Glu Asn Tyr Leu
            340              345              350
His Arg Ile Gly Arg Gly Gly Arg Tyr Gly Val Lys Gly Val Ala Ile
        355              360              365
Asn Phe Val Thr Glu Lys Asp Val Glu Leu Leu His Glu Ile Glu Gly
    370              375              380
His Tyr His Thr Gln Ile Asp Glu Leu Pro Val Asp Phe Ala Ala Tyr
385              390              395                      400
Leu Gly Glu
```

COMPOUNDS AND METHODS FOR THE STIMULATION AND ENHANCEMENT OF PROTECTIVE IMMUNE RESPONSES AND IL-12 PRODUCTION

CROSS-REFERENCE TO RELATED APPLICATION

This application is a continuation-in-part of U.S. patent application Ser. No. 08/232,534, filed Apr. 22, 1994, now abandoned.

TECHNICAL FIELD

The present invention relates generally to compounds and methods for stimulating immune responses in patients, as well as in isolated cells and cell cultures, and for evaluating Leishmania-infected patients. The invention is more particularly related to compounds comprising all or a portion of a *Leishmania braziliensis* antigen (LbeIF4A), which is a homolog of the eukaryotic initiation factor 4A (eIF4A), and to the use of such compounds for stimulating a Th1 immune response.

BACKGROUND OF THE INVENTION

Leishmania are obligate intracellular protozoan parasites of macrophages that cause a spectrum of human diseases, including self-healing skin lesions, diffuse cutaneous and mucosal manifestations, and severe visceral disease. The number of cases of leishmaniasis has increased dramatically in the last 20 years, with about 2 million new cases diagnosed each year. Millions of cases of the disease now exist worldwide, primarily in Brazil, China, East Africa, India and areas of the Middle East. The disease is also endemic in the Mediterranean region, including southern France, Italy, Greece, Spain, Portugal and North Africa.

There are 20 species of Leishmania that infect humans. Of these species, *Leishmania braziliensis* commonly causes localized cutaneous leishmaniasis (CL). Patients with CL have strong delayed-type hypersensitivity (DTH) and in vitro proliferative responses to Leishmania antigens during both active and cured disease. Most patients with CL heal spontaneously. However, in some infected individuals, an active cutaneous disease or mucosal leishmaniasis (ML) arises, which is characterized by severe and progressive destruction of the nasal, oral and/or pharyngeal mucous membranes.

Early diagnosis of leishmaniasis may be critical for successful treatment, but is difficult to achieve since there are no distinctive signs or symptoms of the disease. Parasite detection methods have been used, but such methods are not sensitive or practical. Current serological tests (using, for example, ELISA or immunofluorescence techniques) typically use whole or lysed parasites, and are generally insensitive and prone to cross-reaction with a variety of other diseases. In addition, such methods often fail to detect the potentially fatal disease early enough to allow effective treatment, since they rely on the detection of antibodies that are present during the acute phase of the disease.

In the case of active mucosal disease, the intradermal skin test and lymphocyte proliferative responses to Leishmania antigens are exceptionally strong. In fact, it is possible that tissue destruction associated with mucosal lesions may result in part from a hypersensitivity response to Leishmania antigens. However, the specific antigens involved in the cell-mediated immune response to Leishmania have not been characterized.

Accordingly, there is a need in the art for characterization of Leishmania antigens involved in immune responses, and a determination of their role in disease manifestation. There is also a need to identify improved methods for evaluating patients in the early stages of the disease and for treating leishmaniasis. The present invention fulfills these needs and further provides other related advantages.

SUMMARY OF THE INVENTION

Briefly stated, the present invention provides compounds and methods relating to the Leishmania antigen LbeIF4A, which is homologous to the eukaryotic ribosomal protein eIF4A. In one aspect of the invention, DNA molecules comprising DNA sequences that encode LbeIF4A, or portions or other variants thereof, are provided. Such DNA sequences are selected from the group consisting of: (a) nucleotides 115 through 1323 of SEQ ID NO:1; (b) DNA sequences that hybridize to a nucleotide sequence complementary to nucleotides 115 through 1323 of SEQ ID NO:1 under stringent conditions, wherein the DNA sequence encodes a polypeptide that stimulates a Th1 immune response in peripheral blood mononuclear cells obtained from a Leishmania-infected individual; and (c) DNA that encodes a polypeptide encoded by any of the foregoing DNA sequences.

In related aspects, the present invention provides recombinant expression vectors comprising DNA molecules as described above, host cells transformed or transfected with such expression vectors and a process for preparing a polypeptide encoded by a DNA molecule described above, comprising culturing a transformed or transfected host cell under conditions promoting expression and recovering the polypeptide. Purified polypeptides comprising a sequence of amino acids encoded by a DNA molecule as described above, or amino acids 49–403 of SEQ ID NO:2 (or a variant thereof that differs only in conservative substitutions and/or modifications), are also provided. In addition, monoclonal antibodies that specifically bind such polypeptides are disclosed.

In another aspect, the present invention provides a method for evaluating a patient's capability for generating an immune response, comprising contacting a biological sample obtained from a patient with a polypeptide as described herein and measuring a response of the cells. The biological sample may comprise peripheral blood mononuclear cells, monocytes, B cells, dendritic cells, macrophages or combinations thereof. The response that is measured may be (1) a proliferative response; (2) the secretion of one or more cytokines such as Interferon-γ, Interleukin-2, Interleukin-12 p70, Interleukin-12 p40 subunit, Interleukin-1 or Tumor Necrosis Factor-α; or (3) expression of mRNA encoding one or more cytokines such as Interferon-γ, Interleukin-2, Interleukin-12 p40 subunit, Interleukin-1 or Tumor Necrosis Factor-α.

In yet another aspect, methods for enhancing a cellular and/or humoral immune response to an antigen in a patient are provided, comprising administering a polypeptide as described herein and an antigen to a patient. The polypeptide may be administered in conjunction with a heterologous antigen preparation, or in conjunction with other Leishmania antigens. In a related aspect, the present invention provides methods for stimulating the production of antibodies in a patient that bind to Leishmania parasites, comprising administering to a patient a polypeptide as described herein.

In other aspects, methods are provided for stimulating a Th1 immune response, IL-12 production, and/or the down-regulation of Interleukin-10 expression in a patient, comprising administering to a patient a polypeptide as described herein. In a related aspect, methods are provided for stimulating a Th1 immune response, IL-12 production, and/or the down-regulation of Interleukin-10 expression in a biological sample, comprising contacting the biological sample with a polypeptide as described herein. The biological sample may comprise peripheral blood mononuclear cells, monocytes, B cells, dendritic cells, macrophages or combinations thereof.

In another aspect, this invention provides methods for determining the suitability of an antigen for preparation of a vaccine composition, comprising determining whether the antigen is capable of stimulating the production of Interleukin-12 by cells such as peripheral blood mononuclear cells or macrophages obtained from an individual that is not infected with Leishmania.

Within other aspects, pharmaceutical compositions, comprising a polypeptide as described herein and a physiologically acceptable carrier, and vaccines, comprising a polypeptide as described herein and an antigen, are also provided.

In still another aspect, methods are provided for treating a patient afflicted with a disease responsive to IL-12 stimulation, comprising administering to a patient a polypeptide as described herein.

These and other aspects of the present invention will become apparent upon reference to the following detailed description and attached drawings. All references disclosed herein are hereby incorporated by reference in their entirety as if each was incorporated individually.

DETAILED DESCRIPTION OF THE INVENTION

Figures 1A, 1B:
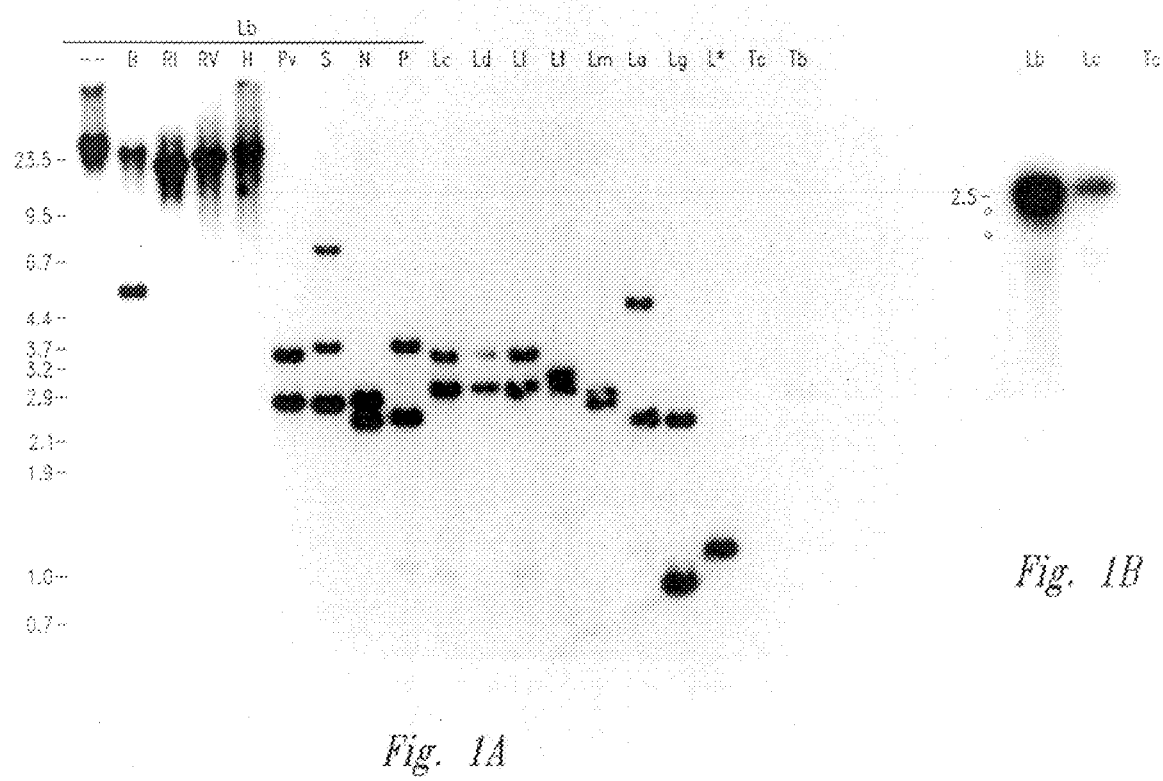
FIG. 1 presents the results of Southern blot analysis of Leishmania spp. DNA, indicating that the Leishmania eIF4A homolog is conserved and that *L. braziliensis* genomic DNA contains at least two copies of LbeIF4A.

As noted above, the present invention is directed to compounds and methods useful for evaluating patients and for stimulating and enhancing immune responses in patients, as well as in isolated cells and cell cultures. The compounds of this invention generally comprise a polypeptide that stimulates a Th1 immune response in peripheral blood mononuclear cells (PBMCs), or a DNA sequence that encodes such a polypeptide. In particular, polypeptides comprising all or a stimulatory portion of a *Leishmania braziliensis* homolog of the eukaryotic ribosomal protein eIF4A (referred to herein as LbeIF4A) are disclosed. As used herein, the term "PBMCs" refers to preparations of nuclear cells that are present in peripheral blood. The term "polypeptide," in the context of this invention, encompasses amino acid chains of any length, including full length proteins and portions thereof, wherein amino acid residues are linked by covalent peptide bonds. Therefore, a "LbeIF4A polypeptide" comprises LbeIF4A, or a portion or other variant thereof that retains stimulatory activity. Preferably, the polypeptides are substantially free of contaminating endogenous materials. The use of such polypeptides for the evaluation of patient immune responses and for the stimulation and enhancement of a variety of immune responses is also disclosed.

The polypeptides of the present invention include variants of LbeIF4A that retain the ability to stimulate a Th1 immune response in PBMCs. Such variants include various structural forms of the primary protein. Due to the presence of ionizable amino and carboxyl groups, for example, a LbeIF4A polypeptide may be in the form of an acidic or basic salt, or may be in neutral form. Individual amino acid residues may also be modified by oxidation or reduction.

Variants within the scope of this invention also include polypeptides in which the primary amino acid structure of LbeIF4A or a fragment thereof is modified by forming covalent or aggregative conjugates with other polypeptides or chemical moieties such as glycosyl groups, lipids, phosphate, acetyl groups and the like. Covalent derivatives may be prepared, for example, by linking particular functional groups to amino acid side chains or at the N- or C-termini. Alternatively, for derivatives in which a polypeptide is joined to a LbeIF4A polypeptide, a fusion protein may be prepared using recombinant DNA, as described below. In one such embodiment, the LbeIF4A polypeptide may be conjugated to a signal (or leader) polypeptide sequence at the N-terminal region of the protein which co-translationally or post-translationally directs transfer of the protein from its site of synthesis to its site of function inside or outside of the cell membrane or wall (e.g., the yeast α-factor leader).

Protein fusions within the present invention may also comprise peptides added to facilitate purification or identification of LbeIF4A polypeptides (e.g., poly-His). For example, the peptide described by Hopp et al., *Bio/Technology* 6:1204 (1988) is a highly antigenic peptide that can be used to facilitate identification. Such a peptide provides an epitope reversibly bound by a specific monoclonal antibody, enabling rapid assay and facile purification of expressed recombinant protein. The sequence of Hopp et al. is also specifically cleaved by bovine mucosal enterokinase, allowing removal of the peptide from the purified protein. Fusion proteins capped with such peptides may also be resistant to intracellular degradation in *E. coli.*

Protein fusions encompassed by this invention further include, for example, LbeIF4A polypeptides linked to an immunoglobulin Fc region. If LbeIF4A fusion proteins are made with both heavy and light chains of an antibody, it is possible to form a protein oligomer with as many as four LbeIF4A protein regions. Also within the scope of the present invention are LbeIF4A polypeptides linked to a leucine zipper domain. Leucine zipper domains are described, for example, in published PCT Application WO 94/10308. LbeIF4A polypeptides comprising leucine zippers may, for example, be oligomeric, dimeric or trimeric. All of the above protein fusions may be prepared by chemical linkage or as fusion proteins, as described below.

The present invention also includes LbeIF4A polypeptides with or without associated native-pattern glycosylation. Polypeptides expressed in yeast or mammalian expression systems may be similar to or slightly different in molecular weight and glycosylation pattern than the native molecules, depending upon the expression system. For instance, expression of DNA encoding LbeIF4A polypeptides in bacteria such as *E. coli* provides non-glycosylated molecules. N-glycosylation sites of eukaryotic proteins are characterized by the amino acid triplet Asn-$A_1$-Z, where $A_1$ is any amino acid except Pro, and Z is Ser or Thr. Variants of LbeIF4A polypeptides having inactivated N-glycosylation sites can be produced by techniques known to those of ordinary skill in the art, such as oligonucleotide synthesis and ligation or site-specific mutagenesis techniques, and are within the scope of this invention. Alternatively, N-linked glycosylation sites can be added to a LbeIF4A polypeptide.

The polypeptides of this invention also include variants of LbeIF4A polypeptides that have an amino acid sequence different from the native LbeIF4A protein because of one or more deletions, insertions, substitutions or other modifications. Such variants should be substantially homologous to the native LbeIF4A and should retain the ability to stimulate a Th1 immune response in PBMCs. "Substantial homology," as used herein, refers to amino acid sequences that may be encoded by DNA sequences that are capable of hybridizing under moderately stringent conditions to a naturally occurring DNA sequence encoding LbeIF4A. Suitable moderately stringent conditions include prewashing in a solution of 5×SSC, 0.5% SDS, 1.0 mM EDTA (pH 8.0); hybridizing at 50° C.–65° C., 5×SSC, overnight; followed by washing twice at 65° C. for 20 minutes with each of 2×, 0.5× and 0.2× SSC containing 0.1% SDS). Such hybridizing DNA sequences are also within the scope of this invention, as are nucleotide sequences that, due to code degeneracy, encode a stimulatory polypeptide that is encoded by a hybridizing DNA sequence. The effect of any such modifications on the activity of a LbeIF4A polypeptide may be readily determined by analyzing the ability of the mutated LbeIF4A peptide to induce a Th1 response using, for example, any of the methods described herein.

Generally, amino acid substitutions should be made conservatively; i.e., a substitute amino acid should replace an amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. Variants within the scope of this invention may also, or alternatively, contain other modifications, including the deletion or addition of amino acids, that have minimal influence on the stimulatory properties, secondary structure and hydropathic nature of the polypeptide. In general, fragments of LbeIF4A may be constructed by deleting terminal or internal residues or sequences. Additional guidance as to suitable modifications may be obtained by a comparison of the sequence of LbeIF4A to the sequences and structures of other eIF4A family members. For example, terminal or internal residues or sequences of LbeIF4A not needed for biological activity may be deleted. Cysteine residues may be deleted or replaced with other amino acids to prevent formation of incorrect intramolecular disulfide bridges upon renaturation. Other approaches to mutagenesis involve modification of adjacent dibasic amino acid residues to enhance expression in yeast systems in which KEX2 protease activity is present.

A LbeIF4A full length protein may generally be obtained using a genomic or cDNA clone encoding the protein. A genomic sequence that encodes full length LbeIF4A is shown in SEQ ID NO:1, and the deduced amino acid sequence is presented in SEQ ID NO:2. Such clones may be isolated by screening an appropriate *Leishmania braziliensis* expression library for clones that express antigens which react with sera from a patient afflicted with mucosal leishmaniasis, and then analyzing the reactive antigens for the ability to stimulate proliferative responses and preferential Th1 cytokine production in patient T cell assays. The library preparation and screen may generally be performed using methods known to those of ordinary skill in the art, such as methods described in Sambrook et al., *Molecular Cloning: A Laboratory Manual*, Cold Spring Harbor Laboratories, Cold Spring Harbor, N.Y., 1989, which is incorporated herein by reference. Briefly, a bacteriophage expression library may be plated and transferred to filters. The filters may then be incubated with serum and a detection reagent. In the context of this invention, a "detection reagent" is any compound capable of binding to the antibody-antigen complex, which may then be detected by any of a variety of means known to those of ordinary skill in the art. Typical detection reagents contain a "binding agent," such as Protein A, Protein G, IgG or a lectin, coupled to a reporter group. Preferred reporter groups include enzymes, substrates, cofactors, inhibitors, dyes, radionuclides, luminescent groups, fluorescent groups and biotin. More preferably, the reporter group is horseradish peroxidase, which may be detected by incubation with a substrate such as tetramethylbenzidine or 2,2'-azino-di-3-ethylbenzthiazoline sulfonic acid. Plaques containing genomic or cDNA sequences that express a protein which binds to an antibody in the serum are isolated and purified by techniques known to those of ordinary skill in the art. Appropriate methods may be found, for example, in Sambrook et al., *Molecular Cloning: A Laboratory Manual*, Cold Spring Harbor Laboratories, Cold Spring Harbor, N.Y., 1989.

Patient T cell assays may generally be performed by treating patient PBMCs with the reactive antigens and analyzing the cells for a suitable response. For example, the PBMC supernatant may be assayed for the level of secreted cytokines. Preferably, the cytokine assayed is Interferon-γ, Interleukin-2, Interleukin-12 (either the p40 subunit or biologically active p70), Interleukin-1 or Tumor Necrosis Factor-α. Cytokines may be assayed, for example, using commercially available antibodies specific for the cytokine of interest in an ELISA format, with positive results determined according to the manufacturer's instructions. Suitable antibodies may be obtained, for example, from Chemicon, Temucula, Calif. and PharMingen, San Diego, Calif. Alternatively, the treated PBMCs may be assayed for mRNA encoding one or more of the cytokines Interferon-γ, Interleukin-2, Interleukin-12 p40 subunit, Interleukin-1 or Tumor Necrosis Factor-α, or the PBMCs may be assayed for a proliferative response as described herein.

Variants of LbeIF4A that retain the ability to stimulate a Th1 immune response in PBMCs may be identified by modifying the sequence in one or more of the aspects described above and assaying the resulting polypeptide for the ability to stimulate a Th1 response. Such assays may generally be performed by treating patient PBMCs with the modified polypeptide and assaying the response, as described above.

The above-described sequence modifications may be introduced using standard recombinant techniques or by automated synthesis of the modified polypeptide. For example, mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide a gene in which particular codons are altered according to the substitution, deletion, or insertion required. Exemplary methods of making the alterations set forth above are disclosed by Walder et al., *Gene* 42:133, 1986; Bauer et al., *Gene* 37:73, 1985; Craik, *BioTechniques*, January 1985, 12–19; Smith et al., *Genetic Engineering: Principles and Methods*, Plenum Press, 1981; and U.S. Pat. Nos. 4,518,584 and 4,737,462.

Mutations in nucleotide sequences constructed for expression of such LbeIF4A polypeptides must, of course, preserve the reading frame of the coding sequences and preferably will not create complementary regions that could hybridize to produce secondary mRNA structures, such as loops or hairpins, which would adversely affect translation of the receptor mRNA. Although a mutation site may be predetermined, it is not necessary that the nature of the mutation per se be predetermined. For example, in order to select for optimum characteristics of mutants at a given site, random mutagenesis may be conducted at the target codon and the expressed LbeIF4A protein mutants screened for the desired activity.

Not all mutations in a nucleotide sequence which encodes a LbeIF4A protein will be expressed in the final product. For example, nucleotide substitutions may be made to enhance expression, primarily to avoid secondary structure loops in the transcribed mRNA (see, e.g., European Patent Application 75,444A), or to provide codons that are more readily translated by the selected host, such as the well-known *E. coli* preference codons for *E. coli* expression.

The polypeptides of the present invention, both naturally occurring and modified, are preferably produced by recombinant DNA methods. Such methods include inserting a DNA sequence encoding a LbeIF4A polypeptide into a recombinant expression vector and expressing the DNA sequence in a recombinant microbial expression system under conditions promoting expression. DNA sequences encoding the polypeptides provided by this invention can be assembled from cDNA fragments and short oligonucleotide linkers, or from a series of oligonucleotides, to provide a synthetic gene which is capable of being inserted in a recombinant expression vector and expressed in a recombinant transcriptional unit.

Recombinant expression vectors contain a DNA sequence encoding a LbeIF4A polypeptide operably linked to suitable transcriptional or translational regulatory elements derived from mammalian, microbial, viral or insect genes. Such regulatory elements include a transcriptional promoter, an optional operator sequence to control transcription, a sequence encoding suitable mRNA ribosomal binding sites, and sequences which control the termination of transcription and translation, as described in detail below. An origin of replication and a selectable marker to facilitate recognition of transformants may additionally be incorporated.

DNA regions are operably linked when they are functionally related to each other. For example, DNA for a signal peptide (secretory leader) is operably linked to DNA for a polypeptide if it is expressed as a precursor which participates in the secretion of the polypeptide; a promoter is operably linked to a coding sequence if it controls the transcription of the sequence; or a ribosome binding site is operably linked to a coding sequence if it is positioned so as to permit translation. Generally, operably linked means contiguous and, in the case of secretory leaders, in reading frame. DNA sequences encoding LbeIF4A polypeptides which are to be expressed in a microorganism will preferably contain no introns that could prematurely terminate transcription of DNA into mRNA.

Expression vectors for bacterial use may comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega Biotec, Madison, Wis. U.S.A.). These pBR322 "backbone" sections are combined with an appropriate promoter and the structural sequence to be expressed. *E. coli* is typically transformed using derivatives of pBR322, a plasmid derived from an *E. coli* species (Bolivar et al., *Gene* 2:95, 1977). pBR322 contains genes for ampicillin and tetracycline resistance and thus provides simple means for identifying transformed cells.

Promoters commonly used in recombinant microbial expression vectors include the β-lactamase (penicillinase) and lactose promoter system (Chang et al., *Nature* 275:615, 1978; and Goeddel et al., *Nature* 281:544, 1979), the tryptophan (trp) promoter system (Goeddel et al., *Nucl. Acids Res.* 8:4057, 1980; and European Patent Application 36,776) and the tac promoter (Maniatis, *Molecular Cloning: A Laboratory Manual*, Cold Spring Harbor Laboratory, p.412, 1982). A particularly useful bacterial expression system employs the phage 1 $P_L$ promoter and cI857ts thermolabile repressor. Plasmid vectors available from the American Type Culture Collection which incorporate derivatives of the 1 $P_L$ promoter include plasmid pHUB2, resident in *E. coli* strain JMB9 (ATCC 37092) and pPLc28, resident in *E. coli* RR1 (ATCC 53082).

Suitable promoter sequences in yeast vectors include the promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., European Patent Application 73,657.

Preferred yeast vectors can be assembled using DNA sequences from pBR322 for selection and replication in *E. coli* (Amp$^r$ gene and origin of replication) and yeast DNA sequences including a glucose-repressible ADH2 promoter and α-factor secretion leader. The ADH2 promoter has been described by Russell et al., *J Biol. Chem.* 258:2674, 1982 and Beier et al., *Nature* 300:724, 1982. The yeast α-factor leader, which directs secretion of heterologous proteins, can be inserted between the promoter and the structural gene to be expressed. See, e.g., Kurjan et al., *Cell* 30:933, 1982; and Bitter et al., *Proc. Natl. Acad. Sci. USA* 81:5330, 1984. The leader sequence may be modified to contain, near its 3' end, one or more useful restriction sites to facilitate fusion of the leader sequence to foreign genes. The transcriptional and translational control sequences in expression vectors to be used in transforming vertebrate cells may be provided by viral sources. For example, commonly used promoters and enhancers are derived from Polyoma, Adenovinis 2, Simian Virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a heterologous DNA sequence. The early and late promoters are particularly useful because both are obtained easily from the virus as a fragment which also contains the SV40 viral origin of replication (Fiers et al., *Nature* 273:113, 1978). Smaller or larger SV40 fragments may also be used, provided the approximately 250 bp sequence extending from the Hind III site toward the Bgl II site located in the viral origin of replication is included. Further, viral genomic promoter, control and/or signal sequences may be utilized, provided such control sequences are compatible with the host cell chosen. Exemplary vectors can be constructed as disclosed by Okayama and Berg, *Mol Cell. Biol.* 3:280, 1983.

A useful system for stable high level expression of mammalian receptor cDNAs in C127 murine mammary epithelial cells can be constructed substantially as described by Cosman et al., *Mol Immunol.* 23:935, 1986. A preferred eukaryotic vector for expression of LbeIF4A protein DNA is pDC406 (McMahan et al., *EMBO J.* 10:2821, 1991), and includes regulatory sequences derived from SV40, human immunodeficiency virus (HIV), and Epstein-Barr virus (EBV). Other preferred vectors include pDC409 and pDC410, which are derived from pDC406. pDC410 was derived from pDC406 by substituting the EBV origin of replication with sequences encoding the SV40 large T antigen. pDC409 differs from pDC406 in that a Bgl II restriction site outside of the multiple cloning site has been deleted, making the Bgl II site within the multiple cloning site unique.

A useful cell line that allows for episomal replication of expression vectors, such as pDC406 and pDC409, which contain the EBV origin of replication, is CV-1/EBNA (ATCC CRL 10478). The CV-L/EBNA cell line was derived by transfection of the CV-1 cell line with a gene encoding Epstein-Barr virus nuclear antigen-I (EBNA-1) and constitutively express EBNA-1 driven from human CMV immediate-early enhancer/promoter.

Transformed host cells are cells which have been transformed or transfected with expression vectors constructed using recombinant DNA techniques and which contain sequences encoding a LbeIF4A polypeptide of the present invention. Transformed host cells may express the desired LbeIF4A polypeptide, but host cells transformed for purposes of cloning or amplifying LbeIF4A DNA do not need to express the LbeIF4A protein. Expressed LbeIF4A proteins will preferably be secreted into the culture supernatant, depending on the DNA selected, but may also be deposited in the cell membrane.

Suitable host cells for expression of recombinant proteins include prokaryotes, yeast or higher eukaryotic cells under the control of appropriate promoters. Prokaryotes include gram negative or gram positive organisms, for example *E. coli* or *bacilli*. Higher eukaryotic cells include established cell lines of insect or mammalian origin as described below. Cell-free translation systems could also be employed to produce LbeIF4A proteins using RNAs derived from the DNA constructs disclosed herein. Appropriate cloning and expression vectors for use with bacterial, fungal, yeast, and mammalian cellular hosts are described, for example, by Pouwels et al., *Cloning Vectors: A Laboratory Manual*, Elsevier, N.Y., 1985.

Prokaryotic expression hosts may be used for expression of LbeIF4A polypeptides that do not require extensive proteolytic and disulfide processing. Prokaryotic expression vectors generally comprise one or more phenotypic selectable markers, for example a gene encoding proteins conferring antibiotic resistance or supplying an autotrophic requirement, and an origin of replication recognized by the host to ensure amplification within the host. Suitable prokaryotic hosts for transformation include *E. coli, Bacillus subtilis, Salmonella typhimurium*, and various species within the genera Pseudomonas, Streptomyces, and Staphylococcus, although other hosts may also be employed.

Recombinant LbeIF4A polypeptides may also be expressed in yeast hosts, preferably from the Saccharomyces species, such as *S. cerevisiae*. Yeast of other genera, such as Pichia or Kluyveromyces may also be employed. Yeast vectors will generally contain an origin of replication from the 2μ yeast plasmid or an autonomously replicating sequence (AR), a promoter, DNA encoding the LbeIF4A polypeptide, sequences for polyadenylation and transcription termination and a selection gene. Preferably, yeast vectors will include an origin of replication and selectable marker permitting transformation of both yeast and *E. coli*, e.g., the ampicillin resistance gene of *E. coli* and the *S. cerevisiae* trp 1 gene, which provides a selection marker for a mutant strain of yeast lacking the ability to grow in tryptophan, and a promoter derived from a highly expressed yeast gene to induce transcription of a structural sequence downstream. The presence of the trp 1 lesion in the yeast host cell genome then provides an effective environment for detecting transformation by growth in the absence of tryptophan.

Suitable yeast transformation protocols are known to those of skill in the art. An exemplary technique described by Hind et al., *Proc. Natl. Acad. Sci. USA* 75:1929, 1978, involves selecting for Trp$^+$ transformants in a selective medium consisting of 0.67% yeast nitrogen base, 0.5% casamino acids, 2% glocose, 10 mg/ml adenine and 20 mg/ml uracil. Host strains transformed by vectors comprising the ADH2 promoter may be grown for expression in a rich medium consisting of 1% yeast extract, 2% peptone, and 1% glucose supplemented with 80 mg/ml adenine and 80 mg/ml uracil. Derepression of the ADH2 promoter occurs upon exhaustion of medium glucose. Crude yeast supernatants are harvested by filtration and held at 4° C. prior to further purification.

Various mammalian or insect (e.g., Spodoptera or Trichoplusia) cell culture systems can also be employed to express recombinant protein. Baculovirus systems for production of heterologous proteins in insect cells are reviewed, for example, by Luckow and Summers, *Bio/Technology* 6:47, 1988. Examples of suitable mammalian host cell lines include the COS-7 lines of monkey kidney cells, described by Gluzman, *Cell* 23:175, 1981, and other cell lines capable of expressing an appropriate vector including, for example, CV-1/EBNA (ATCC CRL 10478), L cells, C127, 3T3, Chinese hamster ovary (CHO), COS, NS-1, HeLa and BHK cell lines. Mammalian expression vectors may comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences.

Purified LbeIF4A polypeptides may be prepared by culturing suitable host/vector systems to express the recombinant translation products of the DNAs of the present invention, which are then purified from culture media or cell extracts. For example, supernatants from systems which secrete recombinant protein into culture media may be first concentrated using a commercially available protein concentration filter, such as an Amicon or Millipore Pellicon ultrafiltration unit. Following the concentration step, the concentrate may be applied to a suitable purification matrix. For example, a suitable affinity matrix may comprise a counter structure protein (i.e., a protein to which LbeIF4A binds in a specific interaction based on structure) or lectin or antibody molecule bound to a suitable support. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred. Gel filtration chromatography also provides a means of purifying LbeIF4A.

Affinity chromatography is a particularly preferred method of purifying LbeIF4A polypeptides. For example, a LbeIF4A polypeptide expressed as a fusion protein comprising an immunoglobulin Fc region can be purified using Protein A or Protein G affinity chromatography. Moreover, a LbeIF4A protein comprising a leucine zipper domain may be purified on a resin comprising an antibody specific to the leucine zipper domain. Monoclonal antibodies against the LbeIF4A protein may also be useful in affinity chromatography purification, by utilizing methods that are well-known in the art.

Finally, one or more reverse-phase high performance liquid chromatography (RP-HPLC) steps employing hydrophobic RP-HPLC media (e.g., silica gel having pendant methyl or other aliphatic groups) can be employed to further purify a LbeIF4A protein composition. Some or all of the foregoing purification steps, in various combinations, can also be employed to provide a homogeneous recombinant protein.

Recombinant LbeIF4A polypeptide produced in bacterial culture is preferably isolated by initial extraction from cell pellets, followed by one or more concentration, salting-out, aqueous ion exchange or size exclusion chromatography steps. High performance liquid chromatography (HPLC) may be employed for final purification steps. Microbial cells employed in expression of recombinant LbeIF4A protein can be disrupted by any convenient method, including freeze-thaw cycling, sonication, mechanical disruption, or use of cell lysing agents.

Fermentation of yeast which express LbeIF4A polypeptide as a secreted protein greatly simplifies purification. Secreted recombinant protein resulting from a large-scale fermentation can be purified by methods analogous to those disclosed by Urdal et al., *J Chromatog.* 296:171, 1984. This reference describes two sequential, reverse-phase HPLC steps for purification of recombinant human GM-CSF on a preparative HPLC column.

Preparations of LbeIF4A polypeptides synthesized in recombinant culture may contain non-LbeIF4A cell components, including proteins, in amounts and of a character which depend upon the purification steps taken to recover the LbeIF4A protein from the culture. These components ordinarily will be of yeast, prokaryotic or non-human eukaryotic origin and preferably are present in innocuous contaminant quantities, on the order of less than about 1 percent by weight. Such preparations are typically free of other proteins which may be normally associated with the LbeIF4A protein as it is found in nature in its species of origin.

Automated synthesis provides an alternative method for preparing polypeptides of this invention having fewer than about 100 amino acids, and typically fewer than about 50 amino acids. For example, the Merrifield solid phase synthesis method may be employed, in which amino acids are sequentially added to a growing amino acid chain. See Merrifield, *J. Am. Chem. Soc.* 85:2149–2146, 1963. Equipment for automated synthesis of polypeptides is commercially available from suppliers such as Applied Biosystems, Inc. of Foster City, Calif.

In addition to the above polypeptides and DNA sequences, the subject invention further provides methods of using the polypeptides disclosed above for evaluating immune responses and for stimulating protective immune responses and IL12 production. It has been found within the present invention that LbeIF4A contains T cell epitope(s) which stimulate PBMCs from Leishmania-infected individuals to proliferate. LbeIF4A also stimulates PBMCs from infected individuals to generate a Th1 cytokine profile. A Th1 response is characterized by the production of the cytokines Interleukin-1 (IL-1), Interleukin-2 (IL-2), Interleukin-12 (IL-12 ) or Interferon-γ (IFN-γ), as well as tumor necrosis factor-α (TNF-α). IL-12 is a heterodimeric molecule comprising p40 and p35 subunits, which must be coexpressed for the production of biologically active IL-12 p70. The p40 subunit is produced only by IL-12-producing cells and is induced in vitro and in vivo after bacterial and parasite stimulation, whereas the p35 subunit is both ubiquitous and constitutively expressed. Therefore, cells producing IL-12 also have a large excess (10–100fold) of biologically inactive free p40 chains.

LbeIF4A also stimulates a Th1 cytokine profile of mRNAs such as those encoding IFN-γ, IL-1, IL-2, IL-12 p40 subunit, and TNF-α, in PBMCs from Leishmania infected patients. No detectable IL-4 or IL-10 mRNA, indicative of a Th2 response, is present in such stimulated PBMCs. In fact, LbeIF4A generally down-regulates the expression of IL-10 mRNA present in the "resting" PBMCs of some leishmaniasis patients as well as the LPS-induced IL-10 production of patient and normal PBMCs. These properties of LbeIF4A suggest a role for LbeIF4A in a protective immune response following L. braziliensis infection.

In addition, LbeIF4A stimulates the production of IL-12 and IL-2 in PBMCs obtained from uninfected control individuals, as well as in cultured human macrophages, in the human myeloid leukemia cell line THP-1 and in mice. LbeIF4A also synergizes with IFN-γ to stimulate THP-1 cells to secrete IL-12, and the induction of IFN-γ production by patient PBMCs is abrogated by the presence of anti-IL-12 antibody. The ability to stimulate IL-12 and IL-2 production indicates that LbeIF4A has the ability to induce a protective immune response, and that the polypeptides described herein have a wide applicability in the prevention and treatment of diseases such as cancer, as well as infectious diseases.

Accordingly, in one aspect of this invention, methods are disclosed for evaluating a patient's overall ability to generate an immune response. As used herein, the term "patient" refers to any warm-blooded animal, preferably a human. A patient may be afflicted with a disease, such as leishmaniasis (or other infectious diseases) or cancer, or may be normal (i.e., free of detectable disease and infection). In general, the level of a proliferative or Th1-associated response elicited upon exposure of a patient's PBMCs to a LbeIF4A polypeptide is indicative of the patient's capacity for generating an immune response.

Briefly, such an evaluation of a patient's ability to generate an immune response may be performed by contacting PBMCs obtained from the patient, who may be infected or uninfected, with a polypeptide of this invention, and measuring a suitable response of the cells. PBMCs for this purpose may be isolated by methods known to those in the art, including by density centrifugation through, for example, Ficoll™ (Winthrop Laboratories, New York). In general, the amount of polypeptide that is sufficient for evaluation of about $10^4$–$10^6$ cells ranges from about 1 μg/ml to about 50 μg/ml, and preferably is about 10 μg/ml. Incubation of polypeptide with PBMCs is typically performed at 37° C. for about five days. Following incubation with polypeptide, the PBMCs are assayed for a suitable response. For example, the response measured may be a proliferative response, which may be evaluated by methods known to those of ordinary skill in the art, such as exposing the cells to a pulse of radiolabeled thymidine and measuring the incorporation of label into cellular DNA. In general, a proliferative response where the stimulation index (i.e., the mean cpm of cells stimulated with antigen divided by the mean cpm of cells without antigen) is greater than or equal to 5 is indicative of an individual with a reduced capacity for generating an immune response. Alternatively, the response measured may be the secretion of one or more specific cytokines (such as IFN-γ, IL-2, IL-12 p70, IL-12 p40 subunit, IL-1 and TNF-α) as described above, or the level of mRNA encoding one or more specific cytokines (such as IFN-γ, IL-2, IL-12 p40 subunit, IL-1 and TNF-α), as determined by techniques well known to those of ordinary skill in the art (which may include amplification by polymerase chain reaction (PCR)). High levels of such cytokine secretion or mRNA expression correspond to a superior capacity for generating an immune response. In general, a patient has a lowered ability to generate an immune response if IL-12, or mRNA encoding IL-12, cannot be detected (by the methods disclosed herein) in PBMCs treated with a LbeIF4A polypeptide.

In further aspects, the present invention provides methods for stimulating immune responses in PBMCs and isolated component cells (including, but not limited to, macrophages, monocytes, B cells and dendritic cells). For stimulation of such cells, the cells may be isolated by any of a variety of techniques well known to those skilled in the art (such as Ficoll-hypaque density centrifugation), and contacted with a LbeIF4A polypeptide in sufficient quantities and for a sufficient time to generate an immune response, as described above. The cells treated according to this invention may (but need not) have been isolated from a patient afflicted with leishmaniasis, or another disorder, and may be reintroduced into a patient after treatment. For cells obtained from Leishmania-infected individuals, the immune responses that may be generated include a preferential Th1 immune response (which includes stimulation of IL-12 production) and the down-regulation of IL-10 expression. For cells from uninfected individuals, the immune response may be the production of IL-12.

In related aspects, the present invention provides methods for stimulating or enhancing immune responses in patients, including humans. In one embodiment, a LbeIF4A polypeptide may be used as an immunomodulating agent to enhance a cellular and/or humoral immune response to a different antigen. By administering a LbeIF4A polypeptide to a patient in combination with a different specific antigen, the patient's immune response to the antigen may be enhanced. In this aspect, the LbeIF4A polypeptide may be administered within the same preparation (e.g., vaccine) as the antigen, or may be administered separately. In general, however, the antigen and the LbeIF4A polypeptide are administered at the same time and site. In this manner, LbeIF4A polypeptides may be used, for example, as adjuvants in vaccine preparations for heterologous agents. Suitable doses and methods of administration are presented in detail below.

LbeIF4A polypeptides may also be administered to Leishmania-infected individuals, either alone or along with other Leishmania antigens to stimulate the production of antibodies that bind to Leishmania parasites. Immunization of mice with LbeIF4A in a model generally recognized as being reasonably predictive of a response to Leishmania species in humans and other mammals has been found to result in a protective immune response against L. braziliensis, confirming the utility of LbeIF4A as a vaccine. The polypeptides of this invention may be administered, for example, to patients suffering from chronic cutaneous leishmaniasis to stimulate a curative immune response.

In further embodiments, the polypeptides disclosed herein may be administered to a patient to generate an immune response. For Leishmania-infected individuals, the immune responses that may be generated include a preferential Th1 immune response (which includes stimulation of IL-12 production) and the down-regulation of IL-10 expression. For uninfected individuals, the immune response may be the production of IL-12 and/or IL-2, or the stimulation of gamma T cells. Suitable doses and methods of administration are as described below.

In yet another aspect of this invention, one or more LbeIF4A polypeptides may be administered to a patient afflicted with a disease responsive to Interleukin-12 stimulation. Such diseases include infections (which may be, for example, bacterial, viral, or protozoan) or diseases such as cancer. In general, the responsiveness of a particular disease to IL-12 stimulation may be determined by evaluating the effect of treatment with a LbeIF4A polypeptide on clinical correlates of immunity. For example, if treatment results in a heightened Th1 response or the conversion of a Th2 to a Th1 profile, with accompanying clinical improvement in the treated patient, the disease is responsive to IL-12 stimulation. Polypeptide administration may be as described below, or may extend for a longer period of time, depending on the indication.

In the above aspects, in which a LbeIF4A polypeptide is used to stimulate or enhance an immune response in a patient, the polypeptide is preferably formulated as a pharmaceutical composition or a vaccine. Pharmaceutical compositions generally comprise one or more LbeIF4A polypeptides in combination with a physiologically acceptable carrier, excipient or diluent. Such carriers will be nontoxic to recipients at the dosages and concentrations employed. The vaccines comprise one or more LbeIF4A polypeptides and one or more additional antigens appropriate for the indication. The use of LbeIF4A proteins in conjunction with soluble cytokine receptors or cytokines is also contemplated.

Routes and frequency of administration and polypeptide doses will vary from individual to individual and may parallel those currently being used in immunization or treatment of other infections. In general, the pharmaceutical compositions and vaccines may be administered by injection (e.g., intramuscular, intravenous or subcutaneous), intranasally (e.g., by aspiration) or orally. The amount and frequency of administration will depend, of course, on such factors as the nature and severity of the indication being treated, the desired response, the condition of the patient, and so forth. Typically, between 1 and 4 doses may be administered for a 2–6 week period. Preferably, two doses are administered, with the second dose 2–4 weeks later than the first. A suitable dose is an amount of LbeIF4A polypeptide that stimulates the production of IL-12 in the patient, such that the amount of IL-12 in supernatants of PBMCs isolated from the patient is between about 10 ng and 10 $\mu$g per mL. In general, the amount of IL-12 may be determined using any appropriate assay known to those of ordinary skill in the art, including the assays described herein. The amount of LbeIF4A polypeptide present in a dose typically ranges from about 1 pg to about 100 mg per kg of host, typically from about 10 pg to about 1 mg, and preferably from about 100 pg to about 1 $\mu$g. Suitable dose sizes will vary with the size of the animal, but will typically range from about 0.01 mL to about 5 mL for 10–60 kg animal. Specific appropriate dosages for a particular indication can be readily determined.

While any suitable carrier known to those of ordinary skill in the art may be employed in the pharmaceutical compositions of this invention, the type of carrier will vary depending on the mode of administration and whether a sustained release administration is desired. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109.

Pharmaceutical compositions and vaccines may also contain diluents such as buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents. Preferably, product is formulated as a lyophilizate using appropriate excipient solutions (e.g., sucrose) as diluents.

Any of a variety of adjuvants may be employed in the vaccines or pharmaceutical compositions of this invention, in addition to the LbeIF4A polypeptide, to nonspecifically enhance the immune response. Most adjuvants contain a substance designed to protect the antigen from rapid catabolism, such as aluminum hydroxide or mineral oil, and a nonspecific stimulator of immune responses, such as lipid A, *Bordella pertussis* or *Mycobacterium tuberculosis*. Such adjuvants are commercially available as, for example, Freund's Incomplete Adjuvant and Complete Adjuvant (Difco Laboratories, Detroit, Mich.) and Merck Adjuvant 65 (Merck and Company, Inc., Rahway, N.J.).

In another aspect of this invention, methods are provided for determining the ability of a given antigen to stimulate a protective immune response. The ability of LbeIF4A to stimulate Interleukin-12 production correlates with the development of a protective, Th1 response in infected patients and PBMCs isolated from infected patients. Therefore, determining whether a selected antigen is capable of stimulating IL-12, IFN-γ and/or IL-2 production provides a rapid, reproducible screening method for use in vaccine development. Antigens that are capable of eliciting a Th1 response, as demonstrated by the stimulation of gamma T cells, IL-12, and/or IL-2 production in normal peripheral blood mononuclear cells using the above-described methods, are generally suitable for preparation of a vaccine.

LbeIF4A protein derivatives may also be used as immunogens, reagents in immunoassays, or as binding agents for affinity purification procedures. LbeIF4A polypeptides for assay or purification purposes may be bound to a solid support. The polypeptide may be bound to the support using a variety of techniques known to those in the art, which are amply described in the patent and scientific literature. In the context of this aspect of the present invention, the term "bound" refers to both noncovalent association, such as adsorption, and covalent attachment (which may be a direct linkage between the antigen and functional groups on the support or may be a linkage by way of a cross-linking agent). Binding by adsorption to a well in a microtiter plate or to a membrane is preferred. In such cases, adsorption may be achieved by contacting the polypeptide, in a suitable buffer, with the solid support for a suitable amount of time. The contact time varies with temperature, but is typically between about 1 hour and 1 day. In general, contacting a well of a plastic microtiter plate (such as polystyrene or polyvinylchloride) with an amount of polypeptide ranging from about 10 ng to about 1 $\mu$g, and preferably about 250 ng, is sufficient to bind an adequate amount of antigen.

The polypeptides may be covalently bound to a solid support using a variety of techniques. For example, binding may be achieved using cross-linking agents, such as M-maleimidobenzoyl succinimide ester and N-hydroxysuccinimide, which covalently bind the polypeptide at cysteine and lysine residues. LbeIF4A polypeptides may also be covalently bound through reactive side groups to various insoluble substrates, such as cyanogen bromideactivated, bisoxirane-activated, carbonyldiimidazole-activated or tosyl-activated agarose structures, or by adsorbing to polyolefin surfaces (with or without glutaraldehyde cross-linking).

Once bound to a substrate, LbeIF4A polypeptides may be used in assays for antibodies that bind the LbeIF4A protein. Suitable assays include enzyme linked immunosorbent assays (ELISAs). Such assays may be performed by first contacting a polypeptide antigen that has been immobilized on a solid support, commonly the well of a microtiter plate, with an antibody-containing sample, such that antibodies to the polypeptide within the sample are allowed to bind to the immobilized polypeptide. Unbound sample is then removed from the immobilized polypeptide and a detection reagent capable of binding to the immobilized antibody-polypeptide complex is added. The amount of detection reagent that remains bound to the solid support is then determined using a method appropriate for the specific detection reagent.

Immobilized polypeptides may also be used to purify antibodies that bind to the LbeIF4A polypeptide. Such antibodies may be prepared by any of a variety of techniques known to those of ordinary skill in the art. See, e.g., Harlow and Land, *Antibodies: A Laboratory Manual*, Cold Spring Harbor Laboratory, 1988. In one such technique, an immunogen comprising the polypeptide is initially injected into any of a wide variety of mammals (e.g., mice, rats, rabbits, sheep and goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for the polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Monospecific antibodies that bind to the polypeptides of this invention may be used, for example, to detect Leishmania infection in a biological sample using one of a variety of immunoassays, which may be direct or competitive. Briefly, in one direct assay format, a monospecific antibody may be immobilized on a solid support (as described above) and contacted with the sample to be tested. After removal of the unbound sample, a second monospecific antibody, which has been labeled with a reporter group, may be added and used to detect bound antigen. In an exemplary competitive assay, the sample may be combined with the monoclonal or polyclonal antibody, which has been labeled with a suitable reporter group. The mixture of sample and antibody may then be combined with polypeptide antigen immobilized on a suitable solid support. Antibody that has not bound to an antigen in the sample is allowed to bind to the immobilized antigen, and the remainder of the sample and antibody is removed. The level of antibody bound to the solid support is inversely related to the level of antigen in the sample. Thus, a lower level of antibody bound to the solid support indicates the presence of Leishmania in the sample. Other formats for using monospecific antibodies to detect Leishmania in a sample will be apparent to those of ordinary skill in the art, and the above formats are provided solely for exemplary purposes.

The following examples are offered by way of illustration, and not by way of limitation. Those skilled in the art will recognize that variations of the invention embodied in the examples can be made, especially in light of the teachings of the various references cited herein.

EXAMPLES

Example 1

Preparation of DNA Encoding LbeIF4A

This example illustrates the molecular cloning of a DNA sequence encoding the *L. braziliensis* ribosomal antigen LbeIF4A.

A genomic expression library was constructed with sheared DNA from *L. braziliensis* (MHOM/BR/75/M2903) in bacteriophage λZAPII (Stratagene, La Jolla, Calif.). The expression library was screened with *E coli*-preadsorbed patient sera from an *L. braziliensis*-infected individual with mucosal leishmaniasis. Plaques containing immunoreactive recombinant antigens were purified, and the pBSK(−) phagemid excised using the manufacturer's protocols. Nested deletions were performed with Exonuclease III to generate overlapping deletions for single stranded template preparations and sequencing. Single stranded templates were isolated following infection with VCSM13 helper phage as recommended by the manufacturer (Stratagene, La Jolla, Calif.) and sequenced by the dideoxy chain terminator method or by the Taq dye terminator system using the Applied Biosystems Automated Sequencer Model 373A.

The immunoreactive recombinant antigens were then analyzed in patient T cell assays for their ability to stimulate a proliferative response, as described in Example 5, below, and a dominant Th1 cytokine profile, as described in Example 7, below.

A recombinant clone was identified in the above assays which, following sequence comparison of its predicted amino acid sequence with sequences of other proteins, was identified as a *Leishmania braziliensis* homolog of the eukaryotic initiation factor 4A (eIF4A). The isolated clone (pLeIF. 1) lacked the first 48 amino acid residues (144 nucleotides) of the full length protein sequence. The pLeIF.1 insert was subsequently used to isolate the full length genomic sequence.

SEQ ID NO:1 shows the entire nucleotide sequence of the full-length LbeIF4A polypeptide. The open reading frame (nucleotides 115 to 1323) encodes a 403 amino acid protein with a predicted molecular weight of 45.3 kD. A comparison of the predicted protein sequence of LbeIF4A with the homologous proteins from tobacco (TeIF4A), mouse (MeIF4A), and yeast (YeIF4A) shows extensive sequence homology, with the first 20–30 amino acids being the most variable. The lengths (403, 413, 407, and 395 amino acids), molecular weights (45.3, 46.8, 46.4, and 44.7 kDa), and isoelectric points (5.9, 5.4, 5.5, and 4.9) of LbeIF4A, TeIF4A, MeIF4A and YeIF4A, respectively, are similar. LbeIF4A shows an overall homology of 75.5% (57% identity, 18.5% conservative substitution) with TeIF4A, 68.6% (50% identity, 18.6% conservative substitution) with MeIF4A and 67.2% (47.6% identity, 19.6% conservative substitution) with YeIF4A.

Example 2

Characterization of the LbeIF4A Gene

This example describes a Southern blot analysis of LbeIF4A DNA in Leishmania species. *Leishmania braziliensis* (MHOM/BR/75/M2903), *L. guyanensis* (MHOM/BR/75/M4147) *L. amazonensis* (IFLA/BR/67/PH8), *L. chagasi* (MHOM/BR/82/BA-2,C1 and MHOM/BR/84/Jonas), *L. donovani* (MHOM/Et/67/HU3), *L. infantum* (IPT-1), *L. major* (LTM p-2), *L. tropica* (1063C), *Trypanosoma cruzi* (MHOM/CH/00/Tulahuen C2) and *T. brucei* (TREU 667) were used and have been previously described (see Burns et al., *Proc. Natl. Acad. Sci. USA*. 90:775–779, 1993). Promastigotes and epimastigotes were cultured in axenic media. *L. chagasi* and *L. amazonensis* amastigotes were obtained from spleens of Syrian hamsters and footpads of BALB/c ByJ mice respectively, and purified as described in Burns et al., *J. Immumol*. 146:742-748, 1991.

Genomic DNA was prepared, digested with enzymes which cut both within (PstI and NotI) and outside of LbeIF4A (BamHI, EcoRI, EcoRV, HindIII, PvuII, and SstI), separated on 0.7% agarose gel and blotted onto Nytran membrane, as described in Sambrook et al., *Molecular Cloning: A Laboratory Manual*, Cold Spring Harbor Laboratory Press, New York, 1989. A restriction fragment comprising a ~0.94 kb fragment (nucleotides 143 to 1083) of the coding region of LbeIF4A was radiolabeled by the random priming method (see Feinberg and Vogelstein, *Anal. Biochem*. 137:266–268, 1984) and blots were hybridized overnight at 65° C. Blots were washed twice at 65° C. for 20 minutes with each of 2×, 0.5× and 0.2× SSC containing 0.1% SDS. *L. braziliensis* genomic DNA contained at least two copies of LbeIF4A as exemplified by the presence of two hybridizing bands in the BamHI and PvuII lanes (FIG. 1).

The same figure also illustrates the cross-species conservation between the eIF4A homolog of *L. braziliensis* and other Leishmania species. Two major PstI hybridizing fragments were detected in all other Leishmania species tested with members of the *L. donovani* complex (*L. chagasi, L. donovani,* and *L. infantum*) showing identical hybridization patterns. LbeIF4A also cross-hybridizes with the more distantly related parasite *T. cruzi* but not *T. brucei* under stringent hybridization conditions. These data show extensive cross-species conservation of the Leishmania eIF4A homolog.

Example 3

Preparation of LbeIF4A

This example illustrates the expression and purification of the ~45 kDa LbeIF4A antigen gene product. The 45 kDa recombinant antigen of the genomic clone pLeIF.1 (i.e., the antigen lacking the N-terminal 48 residues) was purified from 500 ml of IPTG-induced cultures. The inclusion bodies were isolated and sequentially washed in 10 ml TNE (50 mM Tris, pH 8.0, 100 mM NaCl and 10 mM EDTA) containing 2, 4 and 8M urea. Fractions containing solubilized recombinant antigen (usually the 4 and 8M urea supernatants) were pooled, dialyzed against Tris-buffered saline (TBS) and concentrated by precipitation with 30% ammonium sulfate. Purification to homogeneity was accomplished by preparative SDS-PAGE electrophoresis, followed by excision and electroelution of the recombinant antigens. All antigens used in our studies had less than 10 pg/ml endotoxin in a Limulus amebocyte assay performed by Immunex Corp., Seattle, Wash.

The recombinant antigen was used to immunize a rabbit for the production of a polyclonal anti-serum. An adult rabbit (New Zealand White; R & R Rabbitry, Stanwood, Wash.) was immunized by subcutaneous immunization with 100 µg of purified LbeIF4A in incomplete Freund's adjuvant (IFA, GIBCO, Grand Island, N.Y.) together with 100 µg of muramyl dipeptide (adjuvant peptide, Calbiochem-Novabiochem Corp., La Jolla, Calif.), followed by a boost four weeks later with 100 µg of the recombinant antigen in IFA alone. Three weeks later, the rabbit was boosted intravenously with 25 µg of LbeIF4A in saline and serum was collected one week later.

Figure 2:
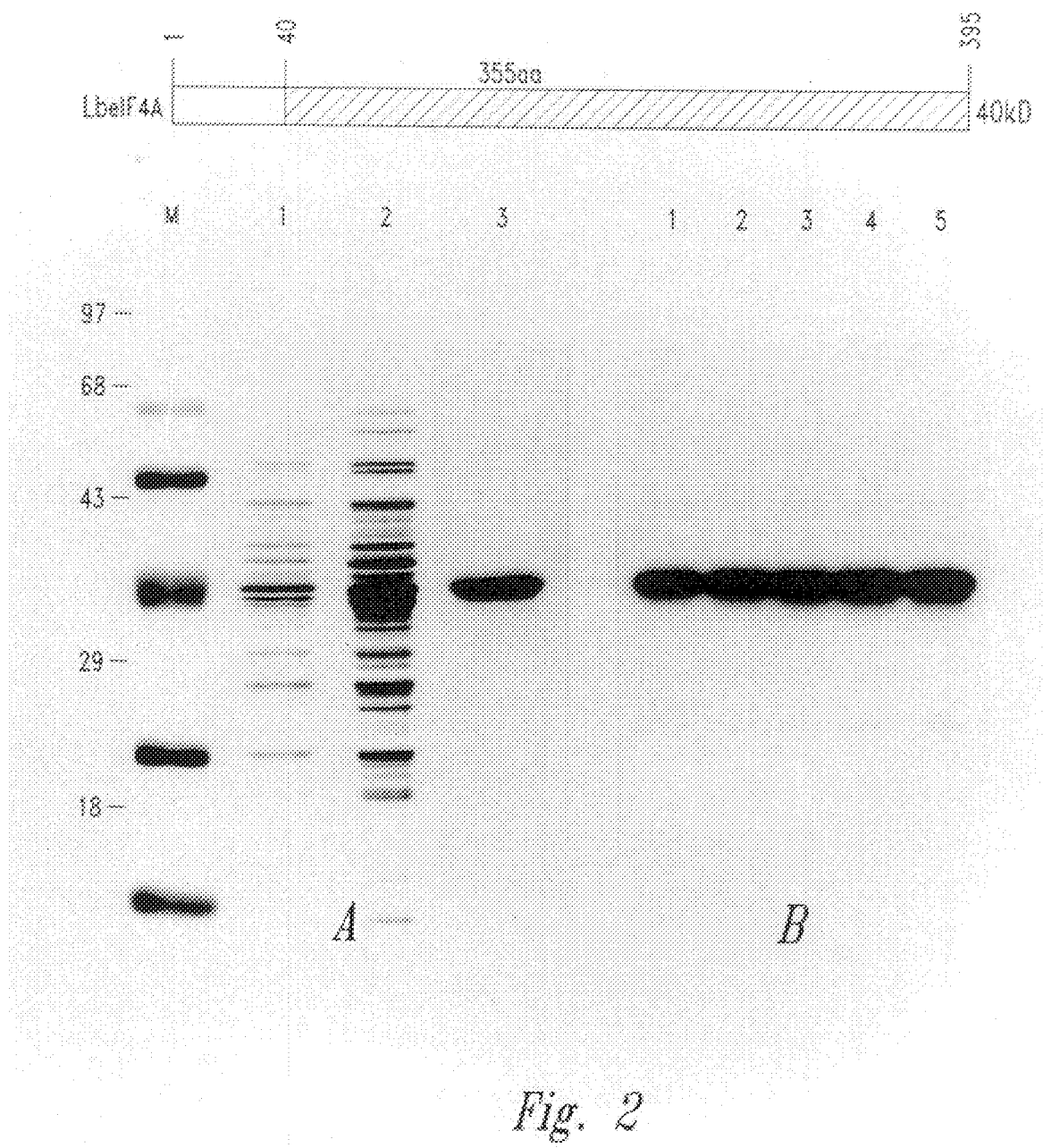
FIG. 2 shows the results of an immunoblot analysis which demonstrates that LbeIF4A immune rabbit serum reacts with one dominant protein species of size ~45 kDa in different Leishmania species.
Figure 3:
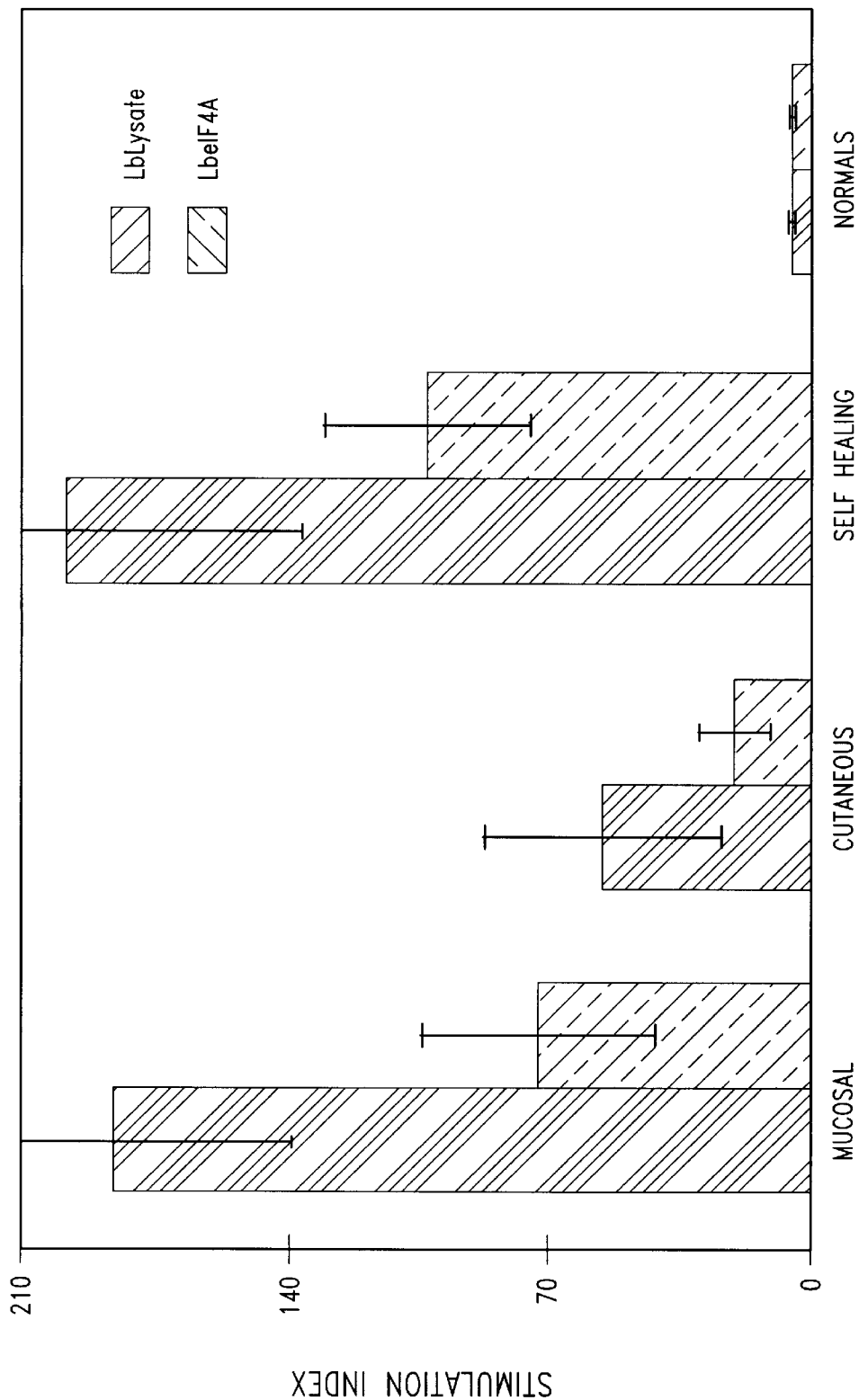
FIG. 3 illustrates the ability of purified recombinant LbeIF4A to stimulate proliferation of PBMCs from *L. braziliensis*-infected individuals.

Immunoblots of *L. braziliensis* lysates from promastigotes harvested during the early-, mid-, or late-log phases or following a temperature shift of the culture from 22°–35° C. were subsequently performed with the polyclonal rabbit anti-serum as a probe (FIG. 2). Panel A of FIG. 2 shows the immunoblot analysis of molecular weight markers (lane M), *E. coli* lysates from uninduced (lane 1) and induced (lane 2) cultures, and the purified recombinant antigen (lane 3). Panel B of FIG. 2 shows the immunoblot analysis of *L. braziliensis* promastigote lysate (lane 1), *L. chagasi* promastigote lysate (lane 2), and *L. amazonensis* promastigote (lane 3) or amastigote (lane 4) lysate.

Parasite and mammalian cell lysates were prepared by freeze/thaw lysis of pellets in SDS sample buffer without glycerol and β-mercaptoethanol. Insoluble material was separated from the supernatant by centrifugation at 10K rpm in a microfuge. Protein concentrations were determined using the Pierce BCA protein assay kit. Five to 10 µg of parasite or cell extracts or 0.5 to 1.0 µg of recombinant antigens were separated on 12.5% SDS-PAGE and transferred electrophoretically to nitrocellulose membranes. Reactivities of the antisera were assessed as previously described (Skeiky et al., *J. Exp. Med.* 176:201–211, 1992) using [$^{125}$I]-Protein A, followed by autoradiography.

The rabbit anti-serum detected one dominant protein species of size ~45 kD. The relative intensities of the 45 kD eIF4A homolog were similar for all the lysates analyzed, thus suggesting that this antigen is constitutively expressed during the early- to mid-log growth phase of the parasite or following a temperature transition that mimics the intracellular amastigote stage. This is unlike members of the Leishmania heat-shock protein family whose products are upregulated following a temperature transition from 22°–35° C. The pre-immune rabbit serum did not react with the parasite lysates.

Example 4

Preparation of Monoclonal Antibodies that Bind to LbeIF4A

This example illustrates the preparation of monoclonal antibodies against LbeIF4A. Preparations of purified recombinant LbeIF4A or transfected cells expressing high levels of LbeIF4A, may be employed to generate monoclonal antibodies against LbeIF4A using conventional techniques, such as those disclosed in U.S. Pat. No. 4,411,993. Such antibodies may be used to interfere with LbeIF4A activation of PBMCs, as components of diagnostic or research assays for LbeIF4A, or in affinity purification of LbeIF4A.

To immunize rodents, LbeIF4A immunogen is emulsified in an adjuvant (such as complete or incomplete Freund's adjuvant, alum, or another adjuvant, such as Ribi adjuvant R700 (Ribi, Hamilton, Mont.), and injected in amounts ranging from 10–100 μg subcutaneously into a selected rodent, for example, BALB/c mice or Lewis rats. Ten days to three weeks days later, the immunized animals are boosted with additional immunogen and periodically boosted thereafter on a weekly, biweekly or every third week immunization schedule. Serum samples are periodically taken by retro-orbital bleeding or tail-tip excision for testing by dot-blot assay (antibody sandwich) or ELISA (enzyme-linked immunosorbent assay). Other assay procedures are also suitable, such as inhibition of the elicitation of a Th1 response.

Following detection of an appropriate antibody titer, positive animals are given an intravenous injection of antigen in saline. Three to four days later, the animals are sacrificed, splenocytes harvested, and fused to a murine myeloma cell line (e.g., NS1 or preferably Ag 8.653 [ATCC CRL 1580]). Hybridoma cell lines generated by this procedure are plated in multiple microtiter plates in a selective medium (for example, one containing hypoxanthine, aminopterin, and thymidine, or HAT) to inhibit proliferation of non-fused cells, myeloma-myeloma hybrids, and splenocyte-splenocyte hybrids.

Hybridoma lines thus generated can be screened by ELISA for reactivity with LbeIF4A, for example, by adaptations of the techniques disclosed by Engvall et al., *Immunochem.* 8:871 (1971) and in U.S. Pat. No. 4,703,004. A preferred screening technique is the antibody capture technique described by Beckman et al., *J. Immunol.* 144:4212 (1990). The hybridoma lines are cloned, for example, by limiting dilution or by cloning in soft agar, to yield a monoclonal cell line. Positive clones are then injected into the peritoneal cavities of syngeneic rodents to produce ascites containing high concentrations (>1 mg/ml) of anti-LbeIF4A monoclonal antibody. The resulting monoclonal antibody can be purified by ammonium sulfate precipitation followed by gel exclusion chromatography. Alternatively, affinity chromatography based upon binding of antibody to protein A or protein G can also be used, as can affinity chromatography based upon binding to LbeIF4A.

Example 5

LbeIF4A Stimulation of PBMC Proliferation

This example illustrates the ability of purified recombinant LbeIF4A to stimulate proliferation of PBMCs from *L. braziliensis*-infected individuals. Peripheral blood was obtained from individuals living in an area (Corte de Pedra, Bahia, Brazil) endemic to *L. braziliensis* transmission where epidemiological, clinical, and immunological studies have been performed for over a decade. Diagnosis of the patients was made by clinical findings associated with at least one of the following: isolation of parasite from lesions, a positive skin test with Leishmania lysate or a positive serological test.

Peripheral blood was collected and PBMCs isolated by density centrifugation through Ficoll™ (Winthrop Laboratories, New York). For in vitro proliferation assays, $2–4\times10^5$ cells/well were cultured in complete medium (RPMI 1640 supplemented with gentamycin, 2-ME, L-glutamine, and 10% screened pooled A+ human serum; Trimar, Hollywood, Calif.) in 96-well flat bottom plates with or without 10 μg/ml of the indicated antigens or 5 μg/ml PHA (Sigma Immunochemicals, St. Louis, Mo.) for five days. The cells were then pulsed with 1 μCi of $[^3H]$ thymidine for the final 18 hours of culture.

Data are represented as mean cpm of triplicate cultures and the stimulation index (SI) defined as mean cpm of cultures with antigens/mean cpm of cultures without antigen. As shown in Table I and FIG. 3, PBMCs from most (>70%) mucosal and active or healed cutaneous patients responded to LbeIF4A with a heterogeneous proliferation pattern with stimulation indices to ranging from 12 to 233 and 2 to 64 respectively.

TABLE I

In Vitro Proliferation of PBMCs from *L. braziliensis*-infected Individuals in Response to Parasite Lysate and LbeIF4A Antigens

| | $[^3H]$Tdr Incorporation (Mean cpm (SD) $\times 10^{-3}$) | | | | |
|---|---|---|---|---|---|
| PATIENTS | MEDIA | LYSATE | S.I. | LbeIF4A | S.I. |
| MUCOSAL | | | | | |
| JV | 0.15 (0.0) | 41.30 (1.3) | 294 | 11.90 (4.8) | 81 |
| SZ | 0.45 (0.1) | 140.60 (7.6) | 308 | 105.90 (5.6) | 233 |
| AB | 0.42 (0.3) | 44.20 (0.5) | 104 | 5.00 (1.3) | 12 |
| NO | 0.38 (0.1) | 52.70 (3.3) | 138 | 12.80 (1.6) | 33 |
| TE | 0.18 (0.0) | 27.40 (1.5) | 150 | 8.80 (0.3) | 48 |
| MB | 0.18 (0.0) | 300.10 (9.4) | 1634 | 41.50 (4.5) | 226 |
| OM | 0.28 (0.0) | 35.40 (3.2) | 124 | 6.90 (2.5) | 24 |

TABLE I-continued

In Vitro Proliferation of PBMCs from *L. braziliensis*-infected Individuals
in Response to Parasite Lysate and LbeIF4A Antigens

[$^3$H]Tdr Incorporation (Mean cpm (SD) × $10^{-3}$)

| PATIENTS | MEDIA | LYSATE | S.I. | LbeIF4A | S.I. |
|---|---|---|---|---|---|
| CUTANEOUS | | | | | |
| AS | 0.22 (0.0) | 19.14 (1.3) | 87 | 14.30 (2.3) | 64 |
| JP | 0.25 (0.0) | 55.63 (8.6) | 218 | 4.40 (0.3) | 17 |
| VS | 0.17 (0.0) | 0.26 (0.0) | 1.5 | 0.3 (0.0) | 2 |
| RJ | 0.10 (0.0) | 0.32 (0.2) | 3.0 | 1.5 (0.6) | 15 |
| JA | 0.16 (0.0) | 0.77 (0.1) | 4.7 | 2.5 (0.2) | 16 |
| AD | 4.20 (1.0) | 4.01 (1.0) | 2.0 | 14.1 (2.2) | 3.5 |
| HN | 0.36 (0.0) | 4.73 (1.7) | 13 | 4.69 (1.7) | 13 |
| DIFFUSE CUTANEOUS | | | | | |
| VAL | 0.22 (0.0) | 0.51 (0.3) | 2.0 | 2.12 (0.2) | 9.0 |
| SELF-HEALING CUTANEOUS | | | | | |
| GS | 0.21 (0.0) | 19.70 (4.4) | 94 | 41.50 (2.8) | 198 |
| MS | 0.09 (0.0) | 0.60 (0.1) | 6.5 | 5.10 (2.1) | 57 |
| AH | 0.11 (0.0) | 59.60 (7.1) | 519 | 9.60 (4.7) | 83 |
| DJ | 0.12 (0.0) | 0.20 (0.1) | 1.6 | 19.00 (6.7) | 151 |
| HS | 0.12 (0.0) | 27.10 (2.0) | 225 | 12.40 (2.7) | 103 |
| MCT | 0.38 (0.0) | 130.30 (14) | 340 | 6.20 (1.5) | 16 |
| NORMAL | | | | | |
| LV | 0.14 (0.0) | 0.19 (0.0) | 1.4 | 0.71 (0.1) | 4.0 |
| VV | 0.18 (0.0) | 0.31 (0.1) | 1.7 | 0.28 (0.1) | 1.5 |
| N3 | 0.14 (0.0) | 0.36 (0.1) | 2.6 | 0.27 (0.1) | 1.9 |
| N4 | 0.59 (0.1) | 2.00 (0.3) | 3.8 | 0.56 (0.0) | 1.0 |

In general, the stimulation indices were higher with PBMCs from mucosal individuals. PBMCs from some mucosal patients responded to LbeIF4A with stimulation indices comparable to those observed with parasite lysate. Interestingly, in some patients with cutaneous leishmaniasis, the proliferative responses to LbeIF4A were higher than those elicited by parasite lysate. In contrast to mucosal and cutaneous patients, PBMCs from all six individuals with self healing cutaneous leishmaniasis proliferated in response to LbeIF4A with stimulation indices (16–198) comparable to those of mucosal individuals. PBMCs from two of the self healing individuals (MS and DJ), had responses that were significantly higher than those obtained with parasite lysate. Cells from normal uninfected individuals were only marginally stimulated by LbeIF4A.

Example 6

LbeIF4A Stimulation of Cytokine mRNA Expression in PBMCs

This example presents an analysis of cytokine mRNA expression patterns of PBMCs from patients with confirmed cases of *L. braziliensis* infection. For cytokine mRNA analysis, 0.5 to 1 μml of PBMCs were cultured at $1-2 \times 10^6$ cells/ml with or without 10 μg/ml of the LbeIF4A antigen lacking the N-terminal 48 residues of SEQ ID NO:2 (as described in Example 3) for 48 and 72 hours. The supernatants and cells were harvested and analyzed for cytokine mRNAs by polymerase chain reaction (PCR). For cytokine mRNA PCR analysis, total RNA was isolated from the PBMCs using the acid guanidium thiocyanate-phenol-chloroform extraction method, as described by Chomczynski and Sacchi, *Anal Biochem.* 162:156–159, 1987. Complementary DNA (cDNA) was synthesized using poly(dT) (Pharmacia) and AMV reverse transcriptase (Bethesda Research Laboratories, Gaithersburg, Md.) in a final volume of 20 μl. cDNA samples were brought to 200 μl with water.

Following normalization to β-actin, 12 to 20 μl of diluted cDNA were amplified by PCR using Taq polymerase (Perkin-Elmer Cetus, Norwalk, Conn.) with 0.2 μM of the respective 5' and 3' external primers in a reaction volume of 50 μl. The conditions used were: denaturation at 94° C. (1 minute for β-actin, IL-2, and IL-4; 45 sec for IFN-γ and 30 sec for IL-10), annealing at 55° C. (1 minute for β-actin, IL-2, and IL-4; 30 sec for IL-10 ) or 60° C. for 45 sec for IFN-γ and elongation at 72° C. We verified that our PCR conditions were within the semi-quantitative range by initially performing serial dilutions of the cDNAs and varying the number of cycles used for PCR. In all subsequent experiments, 30 cycles were used in the amplification reactions for β-actin, IL-2, IL-4, and IFN-γ. In the case of IL-10 PCR, 25 cycles were used.

The primer pairs used and the PCR conditions were from published information; β-actin, IL-2, IL-4 and IFN-γ (Ehlers et al., *J. Exp. Med.* 173:23–36, 1991) and IL-10 (Viera et al., *Proc. Natl. Acad. Sci. U.S.A.* 88:1172–1176, 1991). The nucleotide sequences for the 5' and 3' oligonucleotide primers, respectively, were as follows: (1) β-actin, TGACGGGGTCACCCACACTGTGCCCATCTA and CTAGAAGCATTGCGGTGGACGATGGAGGG; (2) IL-2, ATGTACAGGATGCAACTCCTGTCTT and GTCAGTGT-TGAGATGATGCTTTGAC; (3) IL-4, ATGGGTCTCAC-CTCCCAACTGCT and CGAA-CACTTTGAATATTTCTCTCTCAT; (4) IFN-γ, ATGAAATATACAAGTTATATCTTGGCTTT and GAT-GCTCTTCGACCTCGAAACAGCAT; (5) IL- 10, TCT-CAAGGGGCTGGGTCAGCTATCCCA and ATGC-CCCAAGCTGAGAACCAAGACCCA.

Probes were obtained using plasmids containing the human sequences IL-2, IFN-γ and IL-4 (Lewis et al., *Proc. Natl Acad. Sci. U.S.A.* 85:9743–9747, 1988) and β-actin (no. 65128; American Type Culture Collection, Rockville, Md.), which were digested with HindIII/EcoRI, EcoRI, SacI/

HindII, and EcoRI respectively. Human IL-10 cDNA was cloned by PCR from mitogen-stimulated PBMCs from normal donors using oligonucleotide primers designed to amplify a 535 base pair fragment spanning the entire coding region of human IL-10 (Lewis et al., *Proc. Natl Acad. Sci. U.S.A.* 85:9743–9747, 1988). The cDNA was subcloned into pBluescript and digested with BamHI/EcoRI. After separation on 1% agarose gels, insert DNA fragments were excised, electroeluted, and purified. Radiolabeled $^{32}$P-probes were prepared by the random priming method.

PCR products were analyzed by electrophoresis on 1.5% agarose gels, transferred to nylon membranes, and probed with the appropriate $^{32}$P-labeled DNA insert. Hybridizations were at 55° C. overnight. Post hybridization washes were at 55° C. for 20 minutes twice each with 2×, and 1× SSC containing 0.2% SDS.

Figure 4A:
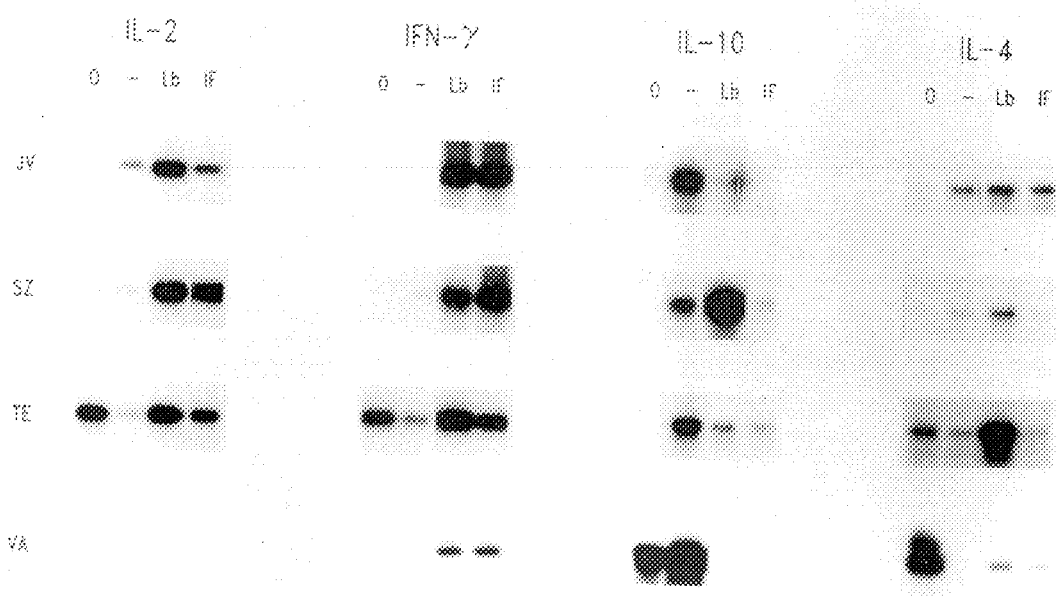
FIGS. 4A and 4B present the results obtained by analysis of cytokine mRNA expression patterns of PBMCs from patients with confirmed cases of *L. braziliensis* infection.
Figure 4B:
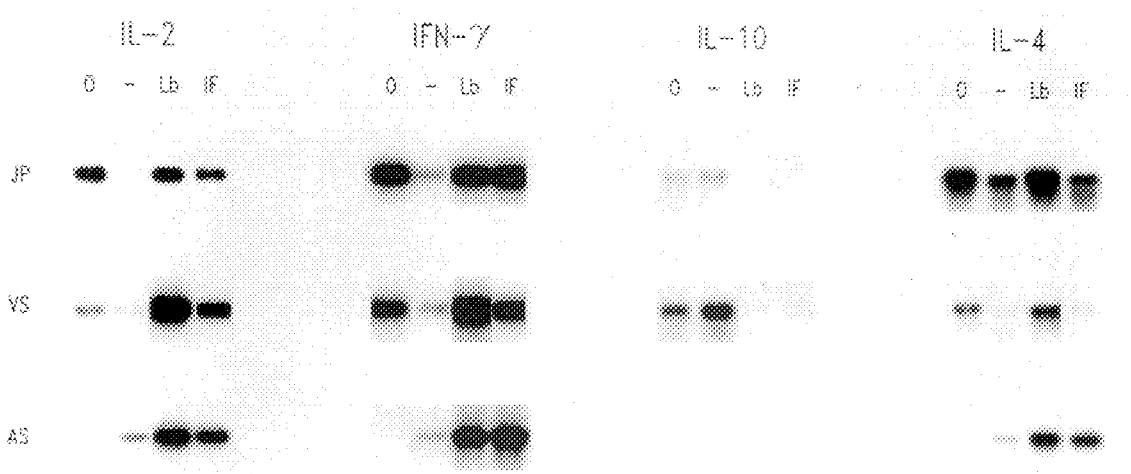

The results of these analyses are presented in FIGS. 4A and 4B. PCR cytokine analyses were performed with cells prior to culturing (lanes 0), following culturing in the absence of antigen (lanes -), or following culturing in the presence of 10 μg/ml *L. braziliensis* lysate (lanes Lb) or in the presence of 10 μg/ml LbeIF4A (lanes IF). FIG. 4A shows the PCR results of cytokine mRNA for three of the six mucosal patients' PBMCs analyzed (JV, SZ, and TE) and one patient (VA) with *L. amazonensis* infection, manifested as diffuse cutaneous leishmaniasis (DCL). In three of the six mucosal patients (TE, FIG. 4A; NO and EO, not shown), PBMCs not cultured in vitro had detectable levels of mRNA for IFN-γ and IL-4, as well as IL-2 (patients TE and EO). IL-10 mRNA was not detected in the "resting" PBMCs from any of the mucosal patients. However, following in vitro culturing in the absence of antigen stimulation, the synthesis of IL-10 mRNA was upregulated in most of the mucosal PBMCs analyzed. In addition, the levels of cytokine mRNAs detected in the "resting" PBMCs of patients TE, NO, and EO, decreased to background levels.

Parasite lysate stimulated the expression of mRNAs of the Th1 cytokines IFN-γ and IL-2 as well as that of the Th2 cytokine IL-4 (in three of the six patients). Increased IL-10 mRNA was detected in one of the patients' PBMCs (SZ) following culture with the parasite lysate. Both LbeIF4A antigen and parasite lysate elicited the production of mRNA of IFN-γ and IL-2 from all mucosal patient PBMCs with LbeIF4A eliciting an exclusive Th1 cytokine profile. In fact, LbeIF4A downregulated the synthesis of IL-10 mRNA detected in the cultured PBMCs of most mucosal patients prior to antigen stimulation. Interestingly, as with the case of using PBMCs from mucosal patients, LbeTF4A also downregulated the synthesis of IL-10 mRNA in the DCL patient VA.

In general, the levels of mRNAs for IFN-γ and IL-2 increased from undetectable amounts prior to antigen stimulation to readily visual levels following antigen stimulation in ethidium bromide stained gels. However, mRNA for the cytokines IL-4 and IL-10, were only detected following radioactive probing of the resolved PCR products.

Similar PCR analysis was performed on PBMCs derived from cutaneous patients (FIG. 4B). The resting PBMCs from three (VS, JP and CA (not shown)) of the four patients analyzed revealed high levels of mRNAs for both the Th1 (IFN-γ and (IL2) and Th2 (IL-4and IL-10) cytokines examined. mRNAs for IFN-γ and IL-2, but not for IL-10 and IL-4, were detected in the resting PBMCs of the fourth (AS) cutaneous patient. Therefore, in contrast to mucosal patients, patients with cutaneous leishmaniasis have IL-10 mRNA, in addition to IL-4, IL-2, and IFN-γ, in their resting PBMCs. Interestingly, while the mRNAs for IL-2 and IFN-γ were reduced to barely detectable levels following the in vitro culturing of PBMCs in the absence of antigen, those for IL-10 remained either unaffected or increased. Therefore, in cutaneous patients, the resting levels of IL-10 mRNA is either stable or their PBMCs continue to synthesize IL-10 mRNA in the absence of antigen stimulation. The observation of such a response for cutaneous leishmaniasis patients can be exploited to differentiate individuals who are predisposed to developing chronic cutaneous leishmaniasis from those who will experience self healing lesions.

All cutaneous patients tested responded to LbeIF4A antigen as well as to the parasite lysate by upregulating the synthesis of mRNAs for IL-2 and IFN-γ and, in two of four patients (VS and AS), the level of IL-4 mRNA also increased following stimulation with parasite lysate. In the three patients (VS, JP and CA) with detectable "resting" levels of IL-10 mRNA, LbeIF4A as well as the parasite lysate downregulated the expression of IL-10, mRNA.

The cytokine mRNA profiles of PBMCs from patients with self-healing CL were similar to those of ML patients in that (a) except for one individual with detectable levels of IL-10 mRNA, resting PBMCs from three of four patients analyzed had detectable levels of IL-2, IFN-γ and IL-4, but little or no IL-10 mRNA; (b) IL-10 mRNA was upregulated after culture of PBMCs without antigen, whereas those of IL-2, IFN-γ and IL-4 decreased to background levels; and (c) leishmanial lysate stimulated the expression of a mixed Th1 /Th2 cytokine profile, whereas LbeIF4A elicited increased mRNA expression of only the Th1-type cytokines and downregulated the expression of IL-10 mRNA in the cultured PBMCs of most self-healing individuals (not shown).

Example 7

LbeIF4A Stimulation of Cytokine Secretion in PBMCs

This example presents the supernatant levels of secreted cytokines of PBMCs from *L. braziliensis*-infected individuals following stimulation with LbeIF4A antigen lacking the N-terminal 48 residues of SEQ ID NO:2 (as described in Example 3) or parasite lysate. Aliquots of the PBMC supernatants were assayed for IFN-γ, TNF-α, IL-4, and IL-10. IFN-γ was quantitated by a double sandwich ELISA using mouse anti-human IFN-γ mAb (Chemicon, Temucula, Calif.) and polyclonal rabbit anti-human IFN-γ serum. Human rIFN-γ (Genentech Inc., San Francisco, Calif.) was used to generate a standard curve. IL-4 was quantitated in supernatants by a double sandwich ELISA using a mouse anti-human IL-4 mAb (M1) and a polyclonal rabbit anti-human IL-4 sera (P3). Human IL-4 (Immunex Corp., Seattle, Wash.) was used to generate a standard curve ranging from 50 pg/ml to 1 ng/ml. IL-10 was measured using a rat anti-human IL-10 mAb (PharMingen, San Diego, Calif., Cat. # 18551D) to "capture" secreted IL-10 and a biotinylated rat antihuman IL-10 mAb (PharMingen San Diego, Calif., Cat. # 18562D) for detection of bound IL-10 with streptavidin conjugated horse radish peroxidase and ABTS as substrate. A standard curve was obtained using human rIL-10 (kindly provided by DNAX Research Institute, Palo Alto, Calif.), ranging from 30 pg to 2 ng/ml.

Figure 5:
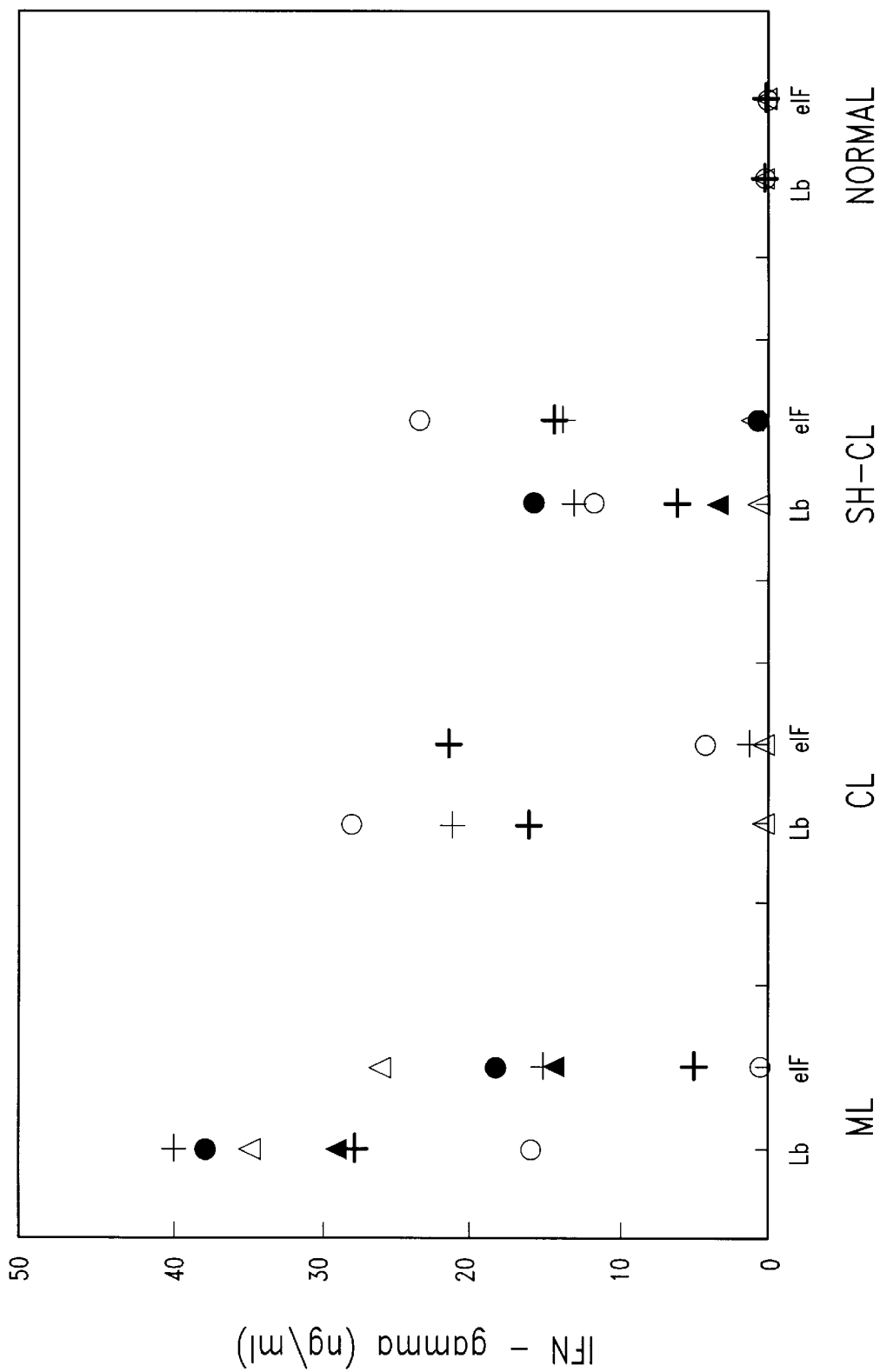
FIG. 5 illustrates the supernatant levels of secreted IFN-γ from PBMCs from *L. braziliensis*-infected individuals following stimulation with LbeIF4A or parasite lysate.
Figure 6:
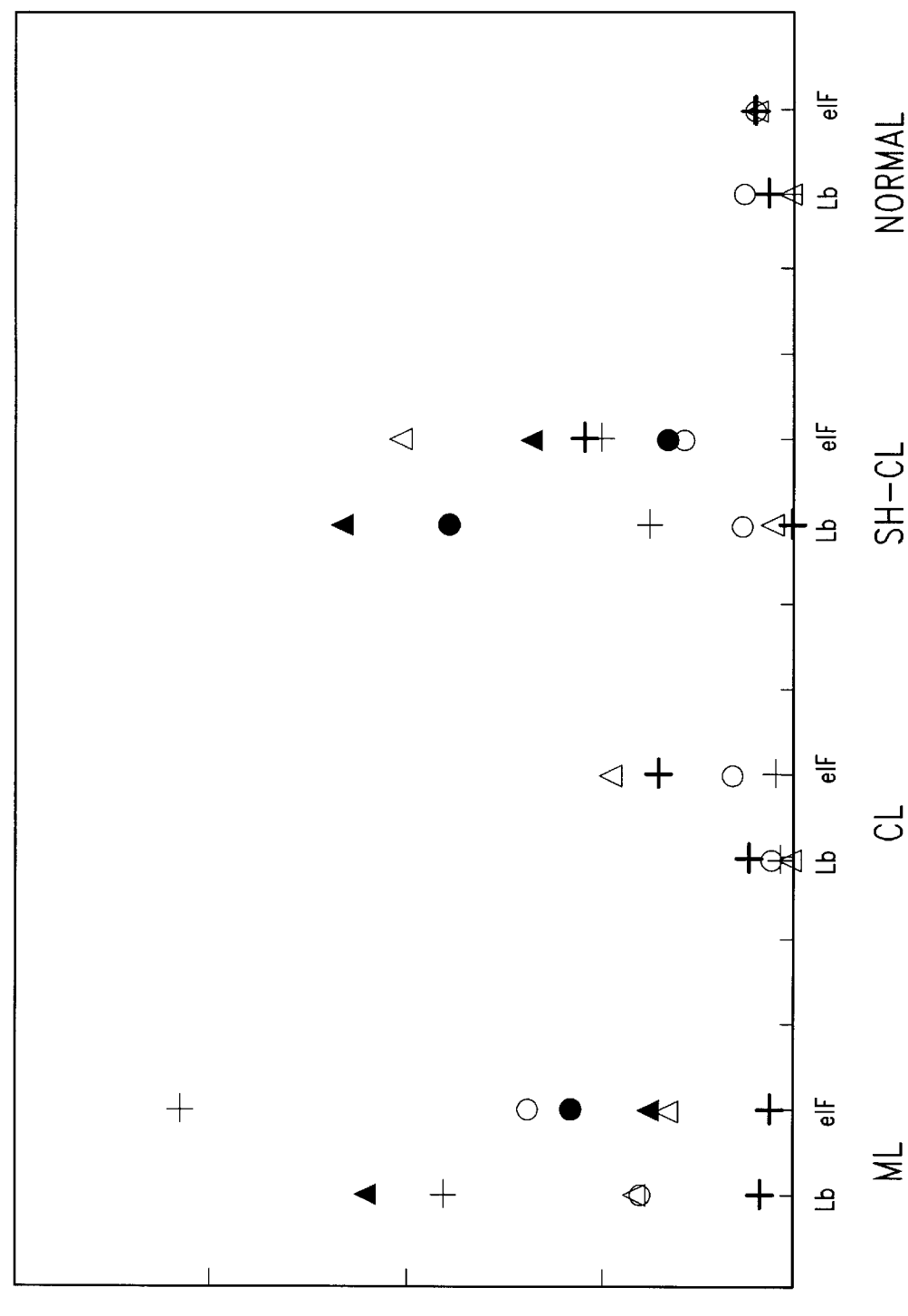
FIG. 6 shows the levels of TNF-α detected in the supernatants of PBMCs from *L. braziliensis*-infected individuals following stimulation with LbeIF4A or parasite lysate.

Cells from all three patient groups (i.e., mucosal, cutaneous and self-healing cutaneous) secreted IFN-γ and TNF-α following stimulation with either 10 μg/ml LbeIF4A antigen or 10 μg/ml parasite lysate (FIGS. 5 and 6). Similarly, LbeIF4A stimulated patients with *L. tropica* infection (Desert Storm Patients) to proliferate and secrete IFN-γ (not shown). The levels of both IFN-γ and TNF-α detected in the supernatants of patient PBMCs were significantly higher than those from uninfected controls. In the absence of antigen stimulation, only PBMCs from mucosal patients (five of six) produced detectable levels of supernatant TNF-α (60 to 190 pg/ml). Little or no IL-4 or IL-10 was detected in any of the supernatants analyzed (not shown), indicating levels below the detection limit of the ELISA assay employed. By comparison, leishmanial lysate also stimulated PBMCs to secrete IFN-γ and TNF-α and, in some patients, IL-10 was also detected (not shown). Taken together, the results demonstrate that LbeIF4A stimulates a predominant Th1 cytokine profile in PBMCs from *L. braziliensis*-infected individuals, whereas parasite lysate stimulates a mixed Th1/Th2 cytokine profile.

The levels of TNF-α detected in the supernatants of patient PBMCs from mucosal and self-healing individuals following antigen stimulation were higher than those from cutaneous patients (FIG. 6). PBMCs from four of five mucosal patients (JV, SZ, AB, and MB) had supernatant levels of TNF-α (0.80 to 2.20 ng/ml) higher than those detected in cultures of PBMCs from uninfected controls following stimulation with parasite lysate. Similarly, the same PBMCs were stimulated by LbeIF4A to produce supernatant levels of TNF-α with values ranging from 0.66 to 3.14 ng/ml. Compared to uninfected controls, PBMCs from three (GS, HS, and MCT) out of six self-healing individuals analyzed produced higher levels of TNF-α in response to parasite lysate, and all six (GS, MS, AH, DJ, HS, and MCT) out of six self-healing individuals analyzed produced higher levels of TNF-α in response to LbeIF4A. The levels of TNF-α produced by PBMCs from cutaneous leishmaniasis patients in response to parasite lysate were comparable to uninfected controls. However, LbeIF4A stimulated PBMCs in three of these patients (RJ, AD and JS) to produce TNF-α. Such patients may be in the process of developing acute cutaneous leishmaniasis.

Example 8

Stimulation of IL-12 Production by LbeIF4A

This example shows that LbeIF4A stimulates PBMCs from *L. braziliensis*-infected individuals, cultured human macrophages, adherent PBMCs from the blood of normal donors and the human myeloid leukemia cell-line THP-1, to secrete IL-12. IL-12 has been shown to play a pivotal immunoregulatory role in the development of cell mediated immunity, generation of Th1 responses and IFN-γ production in intracellular bacterial or parasitic infections. The LbeIF4A polypeptide used was the LbeIF4A antigen lacking the N-terminal 48 residues of SEQ ID NO:2 (as described in Example 3).

IL-12 p40 was measured in cell-free supernatants by RIA (detection limit of 10 pg/ml) using the mAb pairs C11.79/C8.6, as described by D'Andrea et al., *J. Exp. Med.* 179:1387–1398, 1992. Biologically active IL-12 p70 heterodimer (detection limit 1 pg/ml) was measured as described by Kubin et al., *Blood* 83:1847–1855, 1994.

Figure 7A:
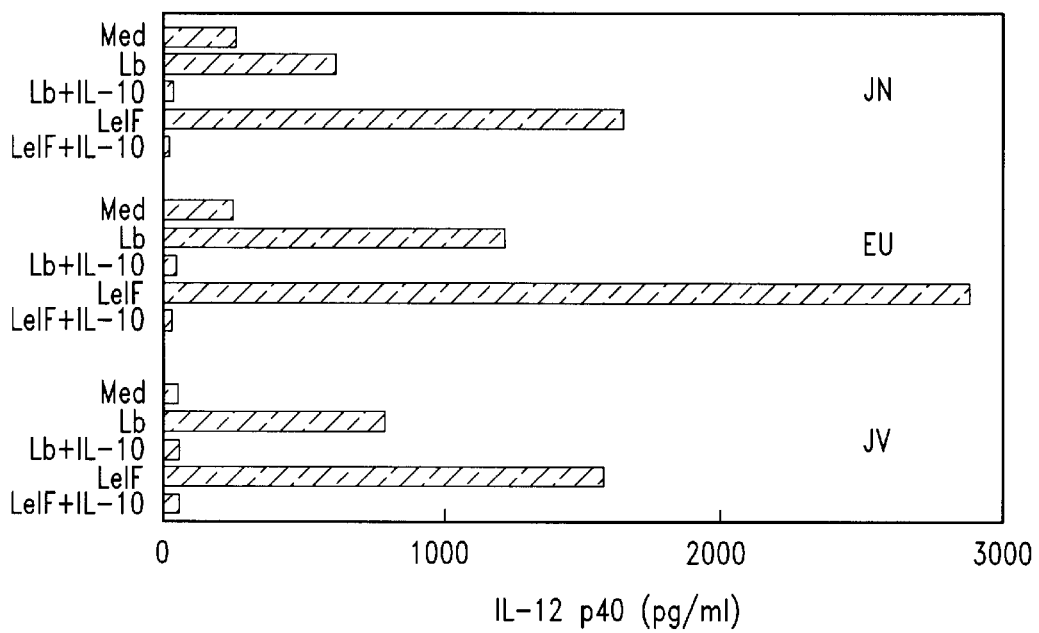
FIG. 7, Panels A–D, shows that LbeIF4A also stimulates patient PBMCs to secrete IL-12 in the cultured supernatant with a magnitude significantly higher than the IL-12 level stimulated by parasite lysate and that IL-10 inhibits this IL-12 production.

FIG. 7A shows that 10 μg/ml LbeIF4A (LeIF) stimulated mucosal patient PBMCs to secrete IL-12 p40 in the cultured supernatant with a magnitude significantly higher than the IL-12 p40 levels observed with 10 μg/ml parasite lysate as antigen (Lb). The amount of IL-12 p40 secreted in the absence of lysate or antigen is also shown (Med.). The same figure also shows that 10 μg/ml IL-10 down-regulated the production of IL-12 p40 by patient PBMCs following stimulation with LbeIF4A (LeIF+IL-10) or lysate (Lb+IL-10).

Figure 7B:
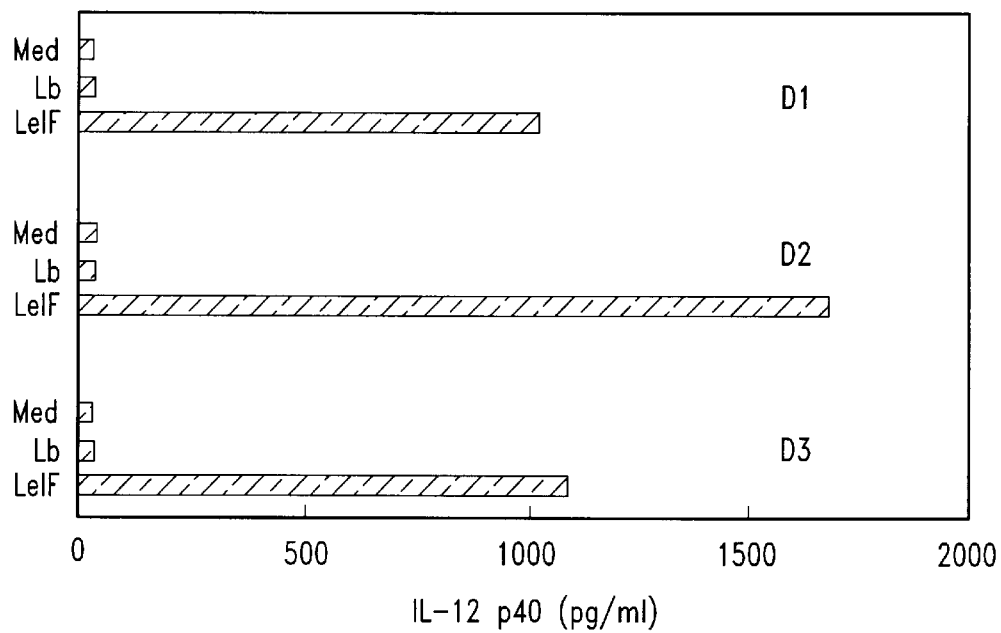

PBMCs from uninfected individuals also produced IL-12 p40 when cultured with LbeIF4A (LeIF, FIG. 7B), although no p40 was detected in response to parasite lysate (Lb). This may suggest a role for IFN-γ in the lysate-induced p40 observed in patient PBMCs, which produced 5–100 fold more IFN-γ than normal PBMCs after antigen stimulation (see FIG. 5).

Figure 7C:
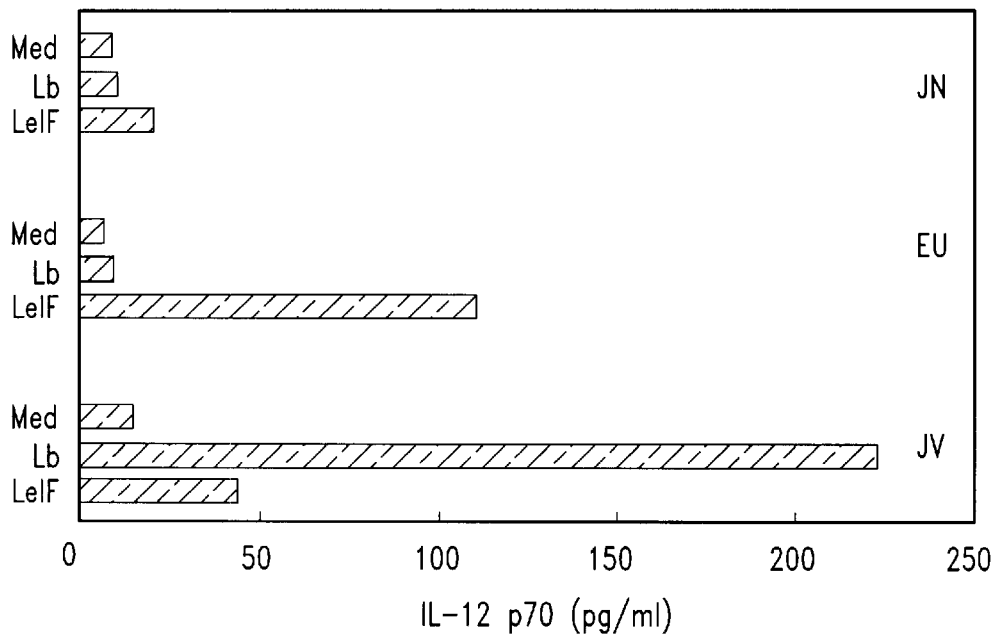
Figure 7D:
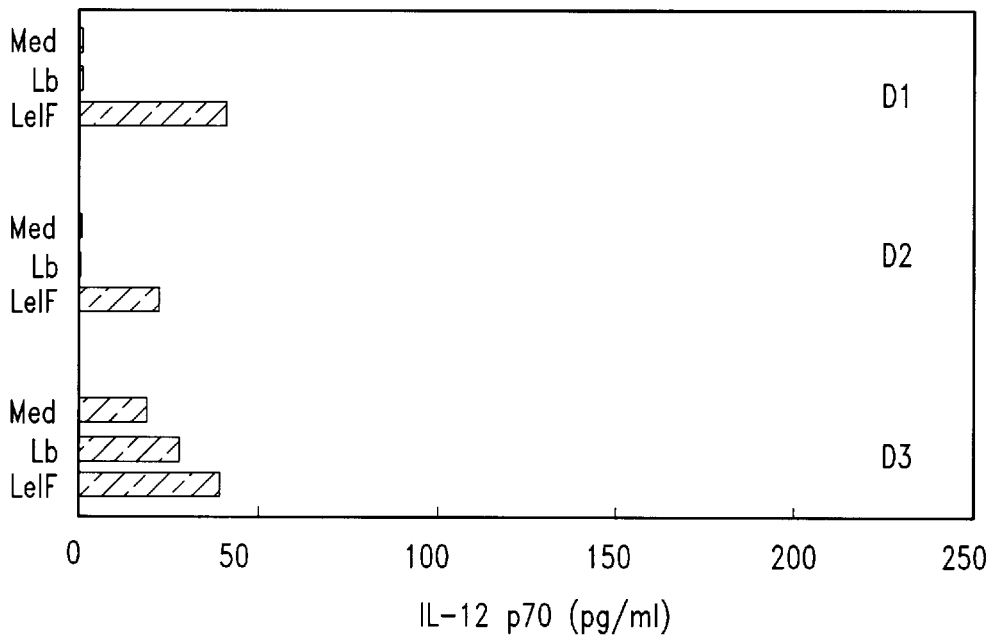

To determine whether the IL-12 p40 observed in antigen-stimulated PBMC cultures reflected biologically active cytokine, IL-12 p70 was also assayed in these cultures (FIGS. 7C and 7D). In general, the p70 production paralleled that of p40, demonstrating that biologically active IL-12 was produced in response to LbeIF4A in both patient and normal PBMCs.

Figure 9A:
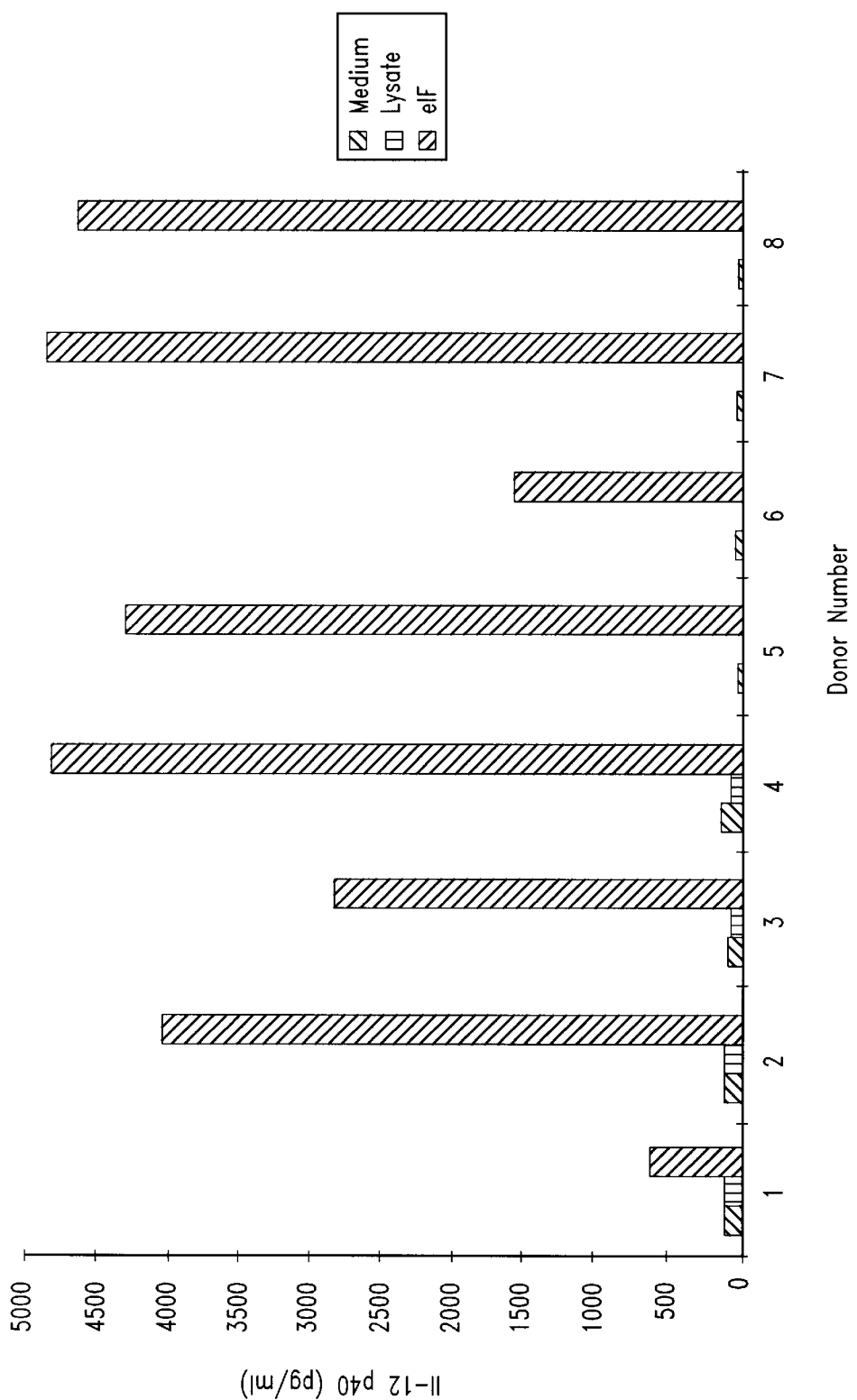
FIGS. 9A and 9B show that LbeIF4A stimulates IL-12 production in cultured human macrophages and adherent PBMCs.
Figure 9B:
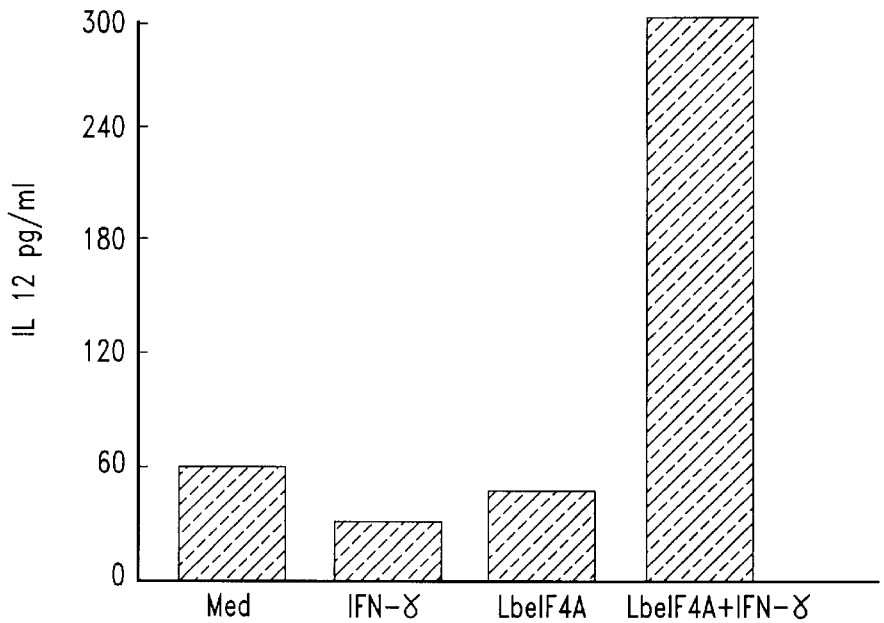

LbeIF4A also stimulates IL-12 production in cultured human macrophages (FIG. 9A) and in adherent PBMCs (FIG. 9B). Adherent cells were prepared from PBMCs separated by Ficoll-hypaque gradient centrifugation from the blood of normal donors. $2\times10^6$ PBMCs were cultivated for 2 hours in 500 μl RPMI, 2% human AB serum. Adherent cells were purified by washing the plates 3 times with PBS. Then 500μl of test medium (RPMI, 2% human AB serum) with the respective stimulus were added (IFN-1000 U/ml, LbeIF4A (Lf) 10 μg/ml). Supernatants were taken after 18 hours.

IL-12 production of adherent PBMCs was measured by a capture bioassay with 5 day old PHA blast. Briefly, the IL-12 capture antibody C11.5.14 (kind gift of the Wistar Institute) was coated on 96 well plates. Supernatants of the induction experiment and recombinant IL-12, as a standard, were incubated for 4 hours. After several wash steps, 5 day old PHA blasts were added and the proliferation of these blasts was used to determine IL-12 concentrations in supernatants of adherent cells.

Macrophages were generated by cultivating adherent cells ($2\times10^6$ PBMCs) for 5 days in test medium. Then, the macrophages were washed in PBS and 500 μl RPMI, 2% human AB serum, and 1000 U/mL IFN-γ was added. Macrophages were stimulated with LbeIF4A (10 μg/ml) or cultivated in medium (M) alone. In one set, LbeIF4A control macrophages were incubated with LbeIF4A in 500 μl RPMI, 2% human AB serum, without IFN-γ. Supernatants were taken after 18 hours and used for induction of IL-12 dependent proliferation. Briefly, 5 day old blasts were incubated with macrophage supernatants for 2 days. For the last 18 hours, $^3$H thymidine was added. Neutralizing anti-IL-12 polyclonal goat serum (5 μg/ml) was added as indicated.

Figure 10:
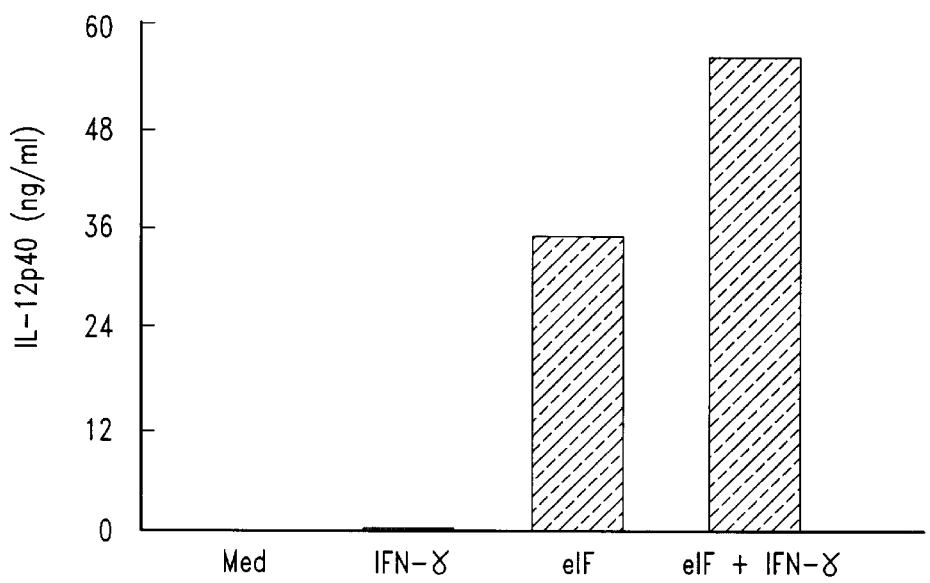
FIG. 10 indicates that LbeIF4A stimulates IL-12 production in the human myeloid leukemia cell-line, THP-1, and synergizes with IFN-γ to stimulate THP1 cells to secrete IL-12.

In addition, LbeIF4A stimulates IL-12 production in the human myeloid leukemia cell-line, THP-1 (FIG. 10). The cells were cultured at $10^6$ cells/mL for 24–48 hours in Endotoxin-free RPMI medium containing 5% Fetal Bovine serum. 10 μg/ml LbeIF4A synergized with IFN-γ to stimulate THP-1 cells to secrete IL-12. These results indicate the utility of LbeIF4A as vaccine.

Example 9

Effect of IL-12 and IL-10 on LbeIF4A Induction of IFN-γ Production

Figure 8A:
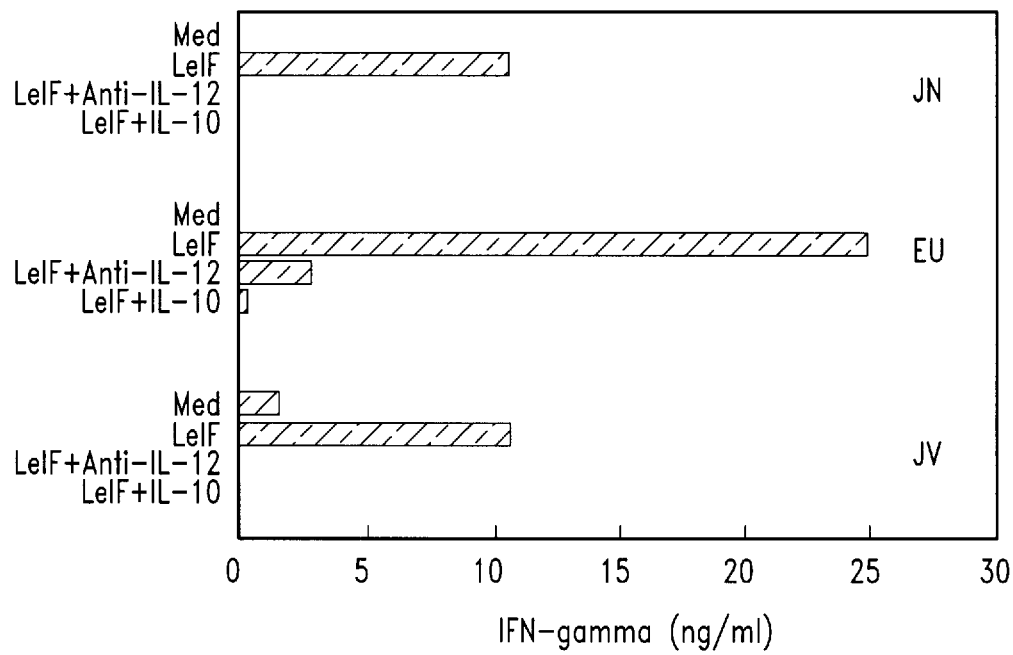
FIG. 8, Panels A and B, demonstrates that in all patient PBMCs tested, IFN-γ production was IL-12 dependent and inhibited by IL-10.
Figure 8B:
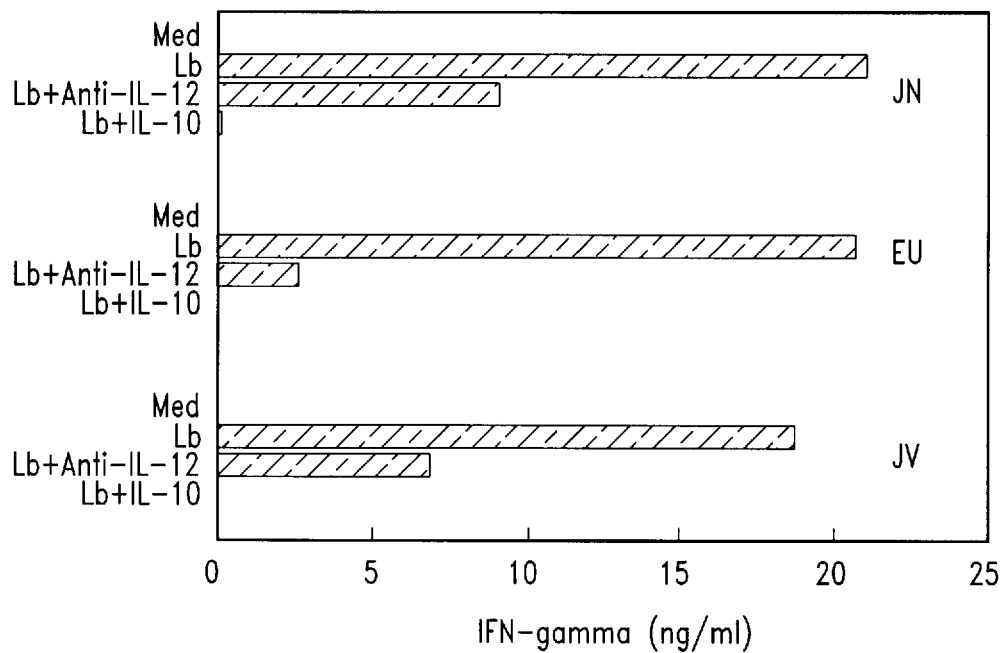

This Example examines the interaction among IL-12, IL-10 and IFN-γ in response to the LbeIF4A polypeptide lacking the N-terminal 48 residues of SEQ ID NO:2 (as described in Example 3). As shown in FIG. 8A, PBMCs from patients with mucosal leishmaniasis were stimulated with 10μg/ml LbeIF4A in the absence (LeIF) or presence of 10 ng/ml anti-IL-12 (LeIF+Anti-IL-12 ), or IL-10 (LeIF+IL-10 ), and the cultured supernatants were assayed for IFN-γ secretion. Both anti-IL-12 mAb and IL-10 abrogated the production of LbeIF4A-induced IFN-γ secretion. However, anti-IL-12 mAb only partially decreased the production of IFN-γ after stimulation with leishmanial lysate (FIG. 8B). These results show that IFN-γ production is IL-12 dependent, and is inhibited by IL-10, whereas the production of IL-12 is regulated by both IFN-γ dependent and independent pathways.

Example 10

LbeIF4A Stimulation of a TH1 Profile in Mice

Figure 11A:
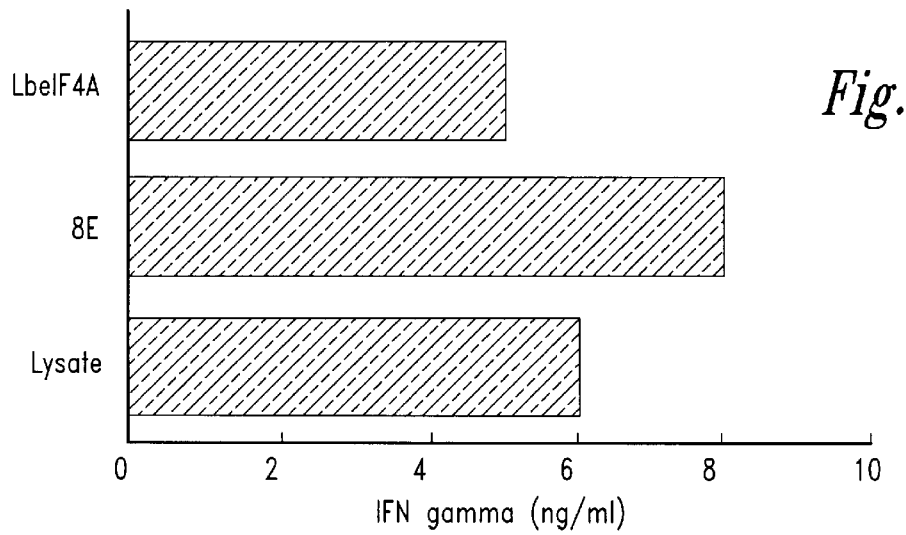
FIG. 11 presents results that indicate that lymph node cells of mice primed with LbeIF4A proliferate and secrete an almost exclusive Th1 cytokine profile, whereas lymph node cells from mice primed with another recombinant *L. braziliensis* antigen (8E) produced a Th0 or Th1/Th2 type cytokine profile, depending upon the adjuvant used, while mice primed with parasite lysate produced a mixed cytokine profile.
Figure 11B:
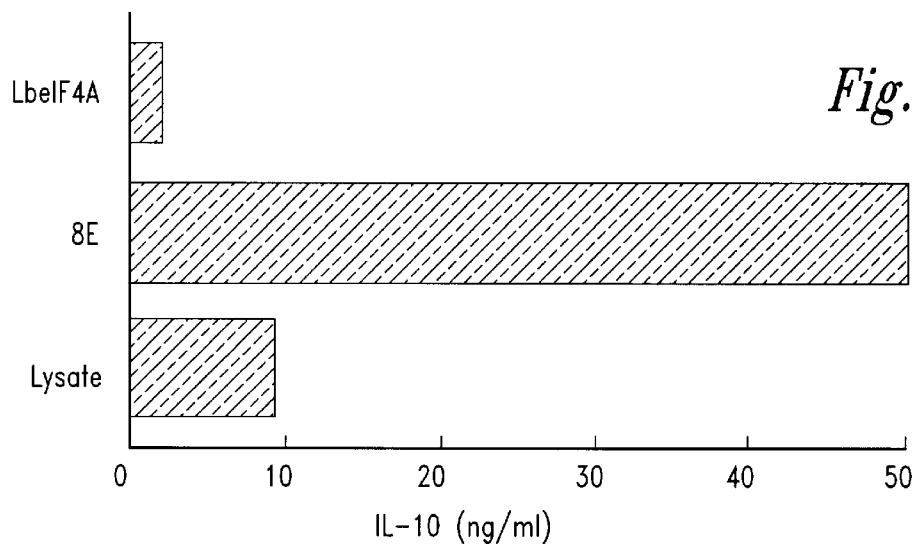
Figure 11C:
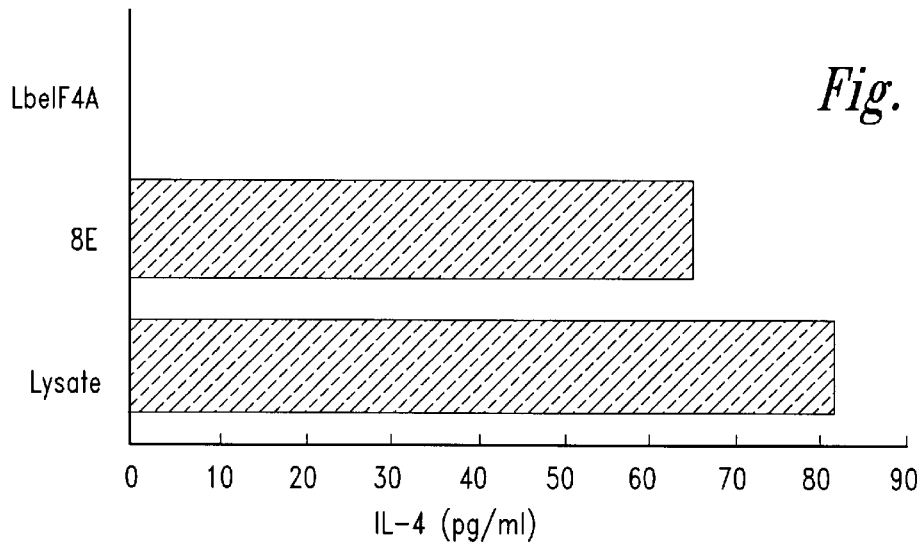

This example demonstrates that the LbeIF4A polypeptide lacking the N-terminal terminal 48 residues of SEQ ID NO:2 (as described in Example 3) stimulates a dominant Th1 cytokine profile in BALB/c mice. The animals were primed with either LbeIF4A or 8E (the C-terminal portion of the *L. braziliensis* mitochondrial hsp70, which stimulates patient PBMCs to produce high levels of IL-10) using quilA or CFA as adjuvants. Ten days after priming, lymph node (LN) cells were restimulated vitro with the recombinant antigens and the supernatant cultures were analyzed for secreted cytokines. The results (FIG. 11) show that LN cells of mice primed with LbeIF4A proliferated and secreted an almost exclusive Th1 cytokine (IFN-γ) following challenge with LbeIF4A using both types of adjuvants. In contrast, LN cells from mice primed with 8E produced a Th0 response with CFA as adjuvant or Th1/Th2 type cytokine (with quilA as adjuvant) with a strong bias towards the Th2 cytokines, IL-4, and IL-10 in specific response to challenge with 8E. Similarly, mice primed with parasite lysate produced a mixed cytokine profile, a result that may argue against the use of parasite lysate alone as vaccine candidate (FIG. 11).

Figure 12:
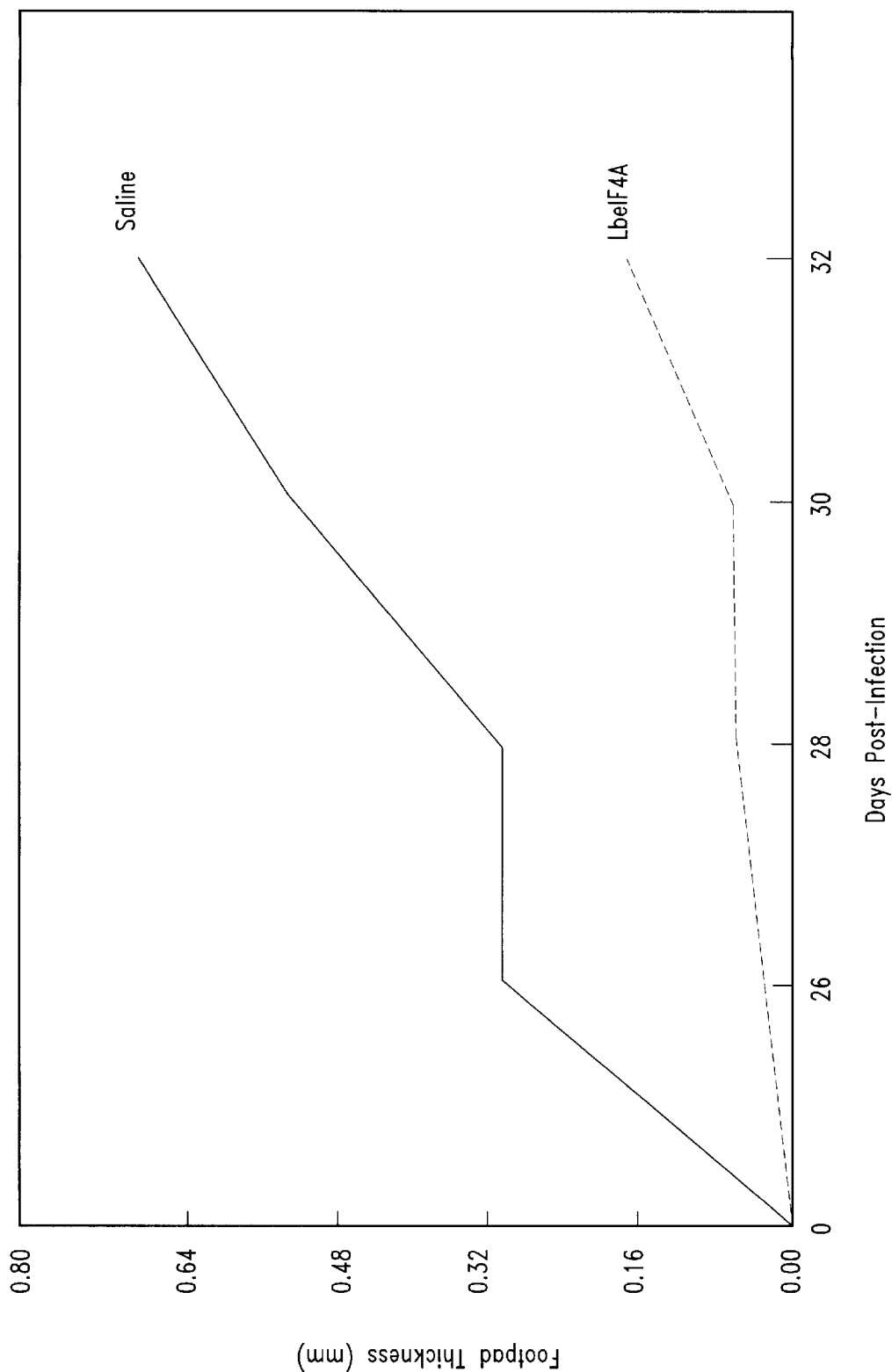
FIG. 12 demonstrates that LbeIF4A provides significant protection against *L. major* infection in an animal model recognized as having relevance to human disease.

These results indicate that LbeIF4A may be used as an adjuvant. Because LbeIF4A induced a powerful Th1 response, including the two cytokines most clearly associated with protection in experimental leishmaniasis, IFN-γ and IL-12, we studied the ability of this antigen to protect mice against leishmaniasis. BALB/c mice were immunized once with LbeIF4A with no adjuvant, followed by subcutaneous infection with *L. major* seven days later. Compared to the control group, LbeIF4A provided significant protection against *L. major* infection (FIG. 12). Thus a heterologous antigen derived from *L. braziliensis* can confer some protection to *L. major* infection, suggesting that, at least some of the "protective" epitopes are conserved between the two parasites.

From the foregoing, it will be appreciated that, although specific embodiments of the invention have been described herein for the purpose of illustration, various modifications may be made without deviating from the spirit and scope of the invention.

---

I claim:

1. A polypeptide comprising an amino acid sequence encoded by a DNA sequence selected from the group consisting of:
   (a) nucleotides 115 through 1323 of SEQ ID NO: 1;
   (b) DNA sequences that hybridize to a nucleotide sequence complementary to nucleotides 115 through 1323 of SEQ ID NO: 1 under moderately stringent conditions, wherein the DNA sequence encodes a polypeptide that stimulates a Th1 immune response in peripheral blood mononuclear cells obtained from a Leishmania-infected individual; and
   (c) DNA that encodes a polypeptide encoded by any of the foregoing DNA sequences.

2. A polypeptide comprising amino acids 49–403 of SEQ ID NO:2.

3. A pharmaceutical composition comprising the polypeptide of either of claims 1 or 2 and a physiologically acceptable carrier.

* * * * *